US011181530B2

(12) United States Patent
Ford et al.

(10) Patent No.: US 11,181,530 B2
(45) Date of Patent: Nov. 23, 2021

(54) MASS SPECTROMETRY METHOD FOR DETECTION AND QUANTITATION OF METABOLITES

(71) Applicant: Metabolon, Inc., Morrisville, NC (US)

(72) Inventors: Lisa Ford, Durham, NC (US); Qibo Zhang, Cary, NC (US); Klaus Peter Adam, Cary, NC (US)

(73) Assignee: Metabolon, Inc., Morrisville, NC (US)

( * ) Notice: Subject to any disclaimer, the term of this patent is extended or adjusted under 35 U.S.C. 154(b) by 88 days.

(21) Appl. No.: 16/305,078

(22) PCT Filed: May 26, 2017

(86) PCT No.: PCT/US2017/034605
§ 371 (c)(1),
(2) Date: Nov. 28, 2018

(87) PCT Pub. No.: WO2017/210097
PCT Pub. Date: Dec. 7, 2017

(65) Prior Publication Data
US 2020/0166519 A1 May 28, 2020

Related U.S. Application Data

(60) Provisional application No. 62/344,613, filed on Jun. 2, 2016.

(51) Int. Cl.
*G01N 33/68* (2006.01)
*G01N 30/72* (2006.01)
(52) U.S. Cl.
CPC ..... *G01N 33/6812* (2013.01); *G01N 30/7233* (2013.01); *G01N 2560/00* (2013.01)

(58) Field of Classification Search
None
See application file for complete search history.

(56) References Cited

U.S. PATENT DOCUMENTS

| 2004/0121305 A1 | 6/2004 | Wiegand et al. |
| 2009/0047269 A1 | 2/2009 | Chinnaiyan et al. |
| 2011/0300571 A1 | 12/2011 | Milburn et al. |

FOREIGN PATENT DOCUMENTS

| WO | 2014012043 A1 | 1/2014 |
| WO | 2014/120449 A1 | 8/2014 |
| WO | 2016/081534 A1 | 5/2016 |

OTHER PUBLICATIONS

CNIPA; Office Action for Chinese Patent Application No. 201780047345.4 dated Nov. 20, 2019, 26 pages.
(Continued)

*Primary Examiner* — Xiaoyun R Xu
(74) *Attorney, Agent, or Firm* — NK Patent Law

(57) ABSTRACT

A method for determining the amount of one or more analytes in a sample by mass spectrometry is described. The one or more analytes are selected from the group consisting of alpha-hydroxybutyrate (2-HB), linoleoyl LPC (LGPC), oleic acid, 3-hydroxybutyrate (3-HB), 4-methyl-2-oxopentanoate (4-MOP), pantothenate, and serine. The method includes a) subjecting the sample to an ionization source under conditions suitable to produce one or more ions detectable by mass spectrometry from each of the one or more of the analytes, wherein the analytes are not derivatized prior to ionization; b) measuring, by tandem mass spectrometry, the amount of the one or more ions from each of the one or more analytes; and c) using the measured amount of the one or more ions to determine the amount of each of the one or more analytes in the sample.

15 Claims, 10 Drawing Sheets

(56) References Cited

OTHER PUBLICATIONS

WIPO; International Preliminary Report on Patentability for International Application No. PCT/US2017/034605 dated Dec. 4, 2018.
ISA/US; International Search Report and Written Opinion for International Application No. WO PCT/US17/34605 dated Oct. 3, 2017, 13 pages.
Cobb, Jeff, et al., "A Novel Test for IGT Utilizing Metabolite Markers of Glucose Tolerance"; Journal of Diabetes Science and Technology 2015, vol. 9(I), pp. 69-76.
Gall, Walter E. et al. "Alpha-Hydroxybutyrate is an Early Biomarker of Insulin Resistance and Glucose Intolerance in a Nondiabetic Population"; PLOS One; May 28, 2010; entire document.
EPO; Extended European Search Report for European Patent Application No. 17807278.1 dated Jan. 14, 2020, 12 pages.
Yan, Zhixiang, et al., "Increase the accessibility and scale of targeted metabolomics: Construction of a human urinary metabolome-wide multiple reaction monitoring library using directly-coupled reversed-phase and hydrophilic interaction chromatography", ELSEVIER, Analytica Chimica Acta, Sep. 24, 2015, pp. 65-75.
Evans, Anne M., et al., "Integrated, nontargeted ultrahigh performance liquid chromatography/electrospray ionization tandem mass spectrometry platform for the identification and relative quantification of the small-molecule complement of biological systems", Analytical Chemistry, Aug. 15, 2009, vol. 81, No. 16, pp. 6656-6667.
CNIPA; Office Action for Chinese Patent Application No. 201780047345.4 dated Jun. 19, 2020, 14 pages.
EPO; Office Action for European Patent Application No. 17807278.1 dated Sep. 11, 2020, 6 pages.
CNIPA; Office Action for Chinese Patent Application No. 201780047345.4 dated Jan. 25, 2021, 13 pages.

MASS SPECTROMETRY METHOD FOR DETECTION AND QUANTITATION OF METABOLITES

CROSS-REFERENCE TO RELATED APPLICATIONS

This application is a U.S. National Stage application of International Application No. PCT/US17/34605, filed May 26, 2017, which claims the benefit of U.S. Provisional Patent Application No. 62/344,613, filed Jun. 2, 2016, the entire contents of which are hereby incorporated herein by reference.

BACKGROUND

The following information to describe the background of the invention is provided to assist the understanding of the invention and is not admitted to constitute or describe prior art to the invention.

Pre-diabetes is associated with obesity and high caloric diets. Pre-diabetes may progress to type 2 diabetes but, if identified early, the progression can be delayed or prevented through lifestyle change and proper nutritional management. Thus, early diagnosis and monitoring of prediabetes is crucial to curtail the type 2 diabetes epidemic. Pre-diabetes is defined clinically using one or more glycemic-based criteria including the levels of fasting plasma glucose (FPG), hemoglobin A1c, and 2-hour plasma glucose measurements from an Oral Glucose Tolerance Test (OGTT). However, these criteria identify only partially overlapping groups of subjects and possibly reflect different pathophysiological states leading to type 2 diabetes. Metabolite-based tests are useful for aiding the diagnosis and assessment of metabolic disorders associated with pre-diabetes and type 2 diabetes, including determination of insulin resistance (IR) and impaired glucose tolerance (IGT). To diagnose prediabetic states such as insulin resistance (IR) and impaired glucose tolerance (IGT) more accurately and earlier, novel metabolite biomarkers have been identified. In particular, seven metabolite biomarkers, 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, and serine measured in blood-based samples such as in plasma or serum have proven useful biomarkers for dysglycemia and pre-diabetes. The amount of one or more of the metabolite biomarkers are informative for diagnosing and monitoring pre-diabetes and for classifying subjects as having impaired glucose tolerance (IGT) and/or insulin resistance (IR). Using amounts of the pre-diabetes biomarkers measured in a blood-based sample, an individual may be diagnosed as having pre-diabetes or a pre-diabetes-related disorder. In addition, an individual having pre-diabetes or a pre-diabetes-related disorder may be monitored by tracking measured levels of the pre-diabetes biomarkers.

Described herein are methods for the detection and quantitation of up to seven analytes in a biological sample. The seven analytes may include 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, and serine. Advantageously, the metabolite assays require a small sample size and can be performed using mass spectrometry analysis methods. The methods may be useful for screening and identifying patients who may have prediabetes, yet may be asymptomatic and/or have normal FPG and hemoglobin A1c results.

The methods described herein to quantitate analytes are more efficient than current methods. Using current methods, at least two separate injections are required to measure all seven analytes. The run time for each injection is more than two minutes. Further, measuring more analytes requires additional instruments and/or additional run time if injections are performed in sequence on the same instrument. The methods described herein allow for measurement of two or more, three or more, four or more, five or more, six or more, or seven analytes in a single sample injection (with the understanding that a single injection is performed on a single instrument) and having a total run time of less than 4 minutes.

SUMMARY

In a first aspect of the invention, a method comprises detecting and determining the amount of one or more analytes selected from the group consisting of 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, and serine, in a sample by mass spectrometry. In methods where amounts of a plurality of analytes are detected, the amounts of the plurality of analytes are detected in a single sample injection. Methods to extract the analytes from biological samples and to chromatographically separate the analytes prior to detection by mass spectrometry are also provided.

In an embodiment wherein the one or more analytes comprise 2-HB, the one or more ions from 2-HB may comprise one or more ions comprising ions with a mass to charge ratio (m/z) of about 103.1±0.5, 57.1±0.5, 35.0±0.5, 44.9±0.5, 55.0±0.5, or 84.9±0.5.

In an embodiment wherein the one or more analytes comprise LGPC, the one or more ions from LGPC may comprise one or more ions comprising ions with a mass to charge ratio (m/z) of about 554.3±0.5, 279.2±0.5, 34.9±0.5, 79.0±0.5, 153.0±0.5, 167.9±0.5, 224.1±0.5, 242.0±0.5, or 504.4±0.5.

In an embodiment wherein the one or more analytes comprise 3-HB, the one or more ions from 3-HB may comprise one or more ions comprising ions with a mass to charge ratio (m/z) of about 103.1±0.5, 59.1±0.5, or 41.1±0.5.

In an embodiment wherein the one or more analytes comprise 4-MOP, the one or more ions from 4-MOP may comprise one or more ions comprising ions with a mass to charge ratio (m/z) of about 129.0±0.5 or 85.1±0.5.

In an embodiment wherein the one or more analytes comprise oleic acid, the one or more ions from oleic acid may comprise one or more ions comprising ions with a mass to charge ratio (m/z) of about 281.3±0.5, 44.7±0.5, 61.8±0.5, 79.8±0.5, 143.1±0.5, 183.0±0.5, 194.9±0.5, 206.9±0.5, 209.0±0.5, 210.1±0.5, 223.1±0.5, 237.1±0.5, or 251.1±0.5.

In an embodiment wherein the one or more analytes comprise pantothenate, the one or more ions from pantothenate may comprise one or more ions comprising ions with a mass to charge ratio (m/z) of about 218.1±0.5, 88.0±0.5, 42.0±0.5, 44.0±0.5, 45.1±0.5, 59.0±0.5, 71.0±0.5, 72.0±0.5, 98.1±0.5, 98.9±0.5, 100.9±0.5, 116.0±0.5, 129.1±0.5, or 146.0±0.5.

In an embodiment wherein the one or more analytes comprise serine, the one or more ions from serine may comprise one or more ions comprising ions with a mass to charge ratio (m/z) of about 104.0±0.5, 74.0±0.5, 40.1±0.5, 42.0±0.5, 45.0±0.5, 56.0±0.5, or 58.1±0.5.

In an embodiment, the method includes determining the amount of a plurality of analytes, such as, for example, the amount of two or more analytes, three or more analytes, four or more analytes, five or more analytes, six or more analytes or seven analytes selected from the group consisting of 2-hydroxybutyric acid (2-HB or AHB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, and serine, in a sample by mass spectrometry using a single injection. Table 10, which is located herein below (after the Examples), lists possible combinations of the 7 analytes. In some related embodiments, the methods further include determining the ratio of the levels of one analyte to another analyte.

In an embodiment, the amount of two or more analytes are determined and at least one of the two or more analytes is selected from the group consisting of 2-HB and LGPC.

In another embodiment, one of the two or more analytes is 2-HB and a second of the two or more analytes is selected from the group consisting of LGPC, 3-HB, 4-MOP, oleic acid, pantothenate, and serine.

In yet another embodiment, one of the two or more analytes is LGPC and a second of the two or more analytes is selected from the group consisting of 2-HB, 3-HB, 4-MOP, oleic acid, pantothenate, and serine.

In an exemplary embodiment, the method includes determining the amount of 2-HB and LGPC in a sample by mass spectrometry using a single injection. In further exemplary embodiments, the method further includes determining the amount of one or more additional analytes selected from the group consisting of 3-HB, 4-MOP, oleic acid, pantothenate, and serine in a sample by mass spectrometry using a single injection. The method includes determining the amount of any of the analytes 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, and serine, alone or in any combination, including combinations of 2 analytes, 3 analytes, 4 analytes, 5 analytes, 6 analytes, and 7 analytes.

In an embodiment, the method includes determining the amount of analytes 2-HB and oleic acid in a sample by mass spectrometry using a single injection. In some embodiments, the method includes determining the amount of one or more additional analytes selected from the group consisting of 3-HB, 4-MOP, LGPC, pantothenate, and serine in a sample by mass spectrometry using a single injection.

In an exemplary embodiment, the method includes determining the amount of analytes 2-HB and 3-HB in a sample by mass spectrometry using a single injection. In some embodiments, the method includes determining the amount of one or more additional analytes selected from the group consisting of LGPC, 4-MOP, oleic acid, pantothenate, and serine in a sample by mass spectrometry using a single injection.

In an exemplary embodiment, the method includes determining the amount of analytes 2-HB and 4-MOP in a sample by mass spectrometry using a single injection. In some embodiments, the method includes determining the amount of one or more additional analytes selected from the group consisting of 3-HB, LGPC, oleic acid, pantothenate, and serine in a sample by mass spectrometry using a single injection.

In an exemplary embodiment, the method includes determining the amount of analytes 2-HB and pantothenate in a sample by mass spectrometry using a single injection. In some embodiments, the method includes determining the amount of one or more additional analytes selected from the group consisting of 3-HB, 4-MOP, oleic acid, LGPC, and serine in a sample by mass spectrometry using a single injection.

In an exemplary embodiment, the method includes determining the amount of analytes 2-HB and serine in a sample by mass spectrometry using a single injection. In some embodiments, the method includes determining the amount of one or more additional analytes selected from the group consisting of 3-HB, 4-MOP, oleic acid, pantothenate, and LGPC in a sample by mass spectrometry using a single injection.

In an exemplary embodiment, the method includes determining the amount of the analytes LGPC and oleic acid in a sample by mass spectrometry using a single injection. In some embodiments, the method includes determining the amount of one or more additional analytes selected from the group consisting of 3-HB, 4-MOP, 2-HB, pantothenate, and serine in a sample by mass spectrometry using a single injection.

In an exemplary embodiment, the method includes determining the amount of analytes LGPC and 3-HB in a sample by mass spectrometry using a single injection. In some embodiments, the method includes determining the amount of one or more additional analytes selected from the group consisting of oleic acid, 4-MOP, 2-HB, pantothenate, and serine in a sample by mass spectrometry using a single injection.

In an exemplary embodiment, the method includes determining the amount of analytes LGPC and 4-MOP in a sample by mass spectrometry using a single injection. In some embodiments, the method includes determining the amount of one or more additional analytes selected from the group consisting of 3-HB, oleic acid, 2-HB, pantothenate, and serine in a sample by mass spectrometry using a single injection.

In an exemplary embodiment, the method includes determining the amount of analytes LGPC and pantothenate in a sample by mass spectrometry using a single injection. In some embodiments, the method includes determining the amount of one or more additional analytes selected from the group consisting of 3-HB, 4-MOP, 2-HB, oleic acid, and serine in a sample by mass spectrometry using a single injection.

In an exemplary embodiment, the method includes determining the amount of analytes LGPC and serine in a sample by mass spectrometry using a single injection. In some embodiments, the method includes determining the amount of one or more additional analytes selected from the group consisting of 3-HB, 4-MOP, 2-HB, pantothenate, and oleic acid in a sample by mass spectrometry using a single injection.

In an embodiment, the method comprises measuring the amount of a plurality of analytes having differences in polarity in a single injection using a separation step followed by MS detection. For example, serine differs in polarity from 2-HB, 3-HB, 4-MOP, LGPC, and oleic acid. A submicron UPLC column and reversed phase chromatography conditions may be used to allow for measuring the amount of serine in combination with one or more analytes selected from the group consisting of 2-HB, 3-HB, 4-MOP, LGPC, and oleic acid, in a single injection. In another example, pantothenate differs in polarity from 2-HB, 3-HB, 4-MOP, LGPC, and oleic acid. A submicron UPLC column and reversed phase chromatography conditions may be used to allow for measuring the amount of pantothenate in combination with one or more analytes selected from the group consisting of 2-HB, 3-HB, 4-MOP, LGPC, and oleic acid, in a single injection.

In embodiments, the sample may be a plasma sample or a serum sample. The sample may be collected using EDTA-plasma tubes or lithium heparin plasma tubes. The sample volume may be 10 µl to 200 µl. For example, the sample volume may be 10 µl, 15, 20, 25, 30, 40, 50 µl, 60, 70, 80, 90, 100, 120, 140, 160, 180 or 200 µl or any other volume between 10 and 200 µl.

In some embodiments, the method comprises measuring a plurality of analytes while also obtaining separation of the critical pair 4-MOP and 3-MOP (see FIG. 8A, retention time of 1.09 and 1.04 minutes, respectively).

In an embodiment, the method run time is less than 3 minutes. For example, the method run time is about 2 minutes. In a further example, the method run time is about 2.21 minutes.

In embodiments, one or more separately detectable internal standards is provided in the sample, the amount of which is also determined in the sample. In these embodiments, all or a portion of one or more endogenous analytes selected from the group consisting of 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid, pantothenate, serine, and the one or more internal standards present in the sample are ionized to produce a plurality of ions detectable in a mass spectrometer. In some embodiments, the amount of ions generated from an analyte of interest may be related to the presence of amount of analyte of interest in the sample by comparison to one or more internal standards.

In some embodiments, the amount of an analyte in a sample may be determined by comparison of the amount of one or more analyte ions detected by mass spectrometry to the amount of one or more standard ions detected by mass spectrometry in an external reference standard. Exemplary external reference standards may comprise blank plasma or serum spiked with a known amount of one or more of the above-described internal standards and/or analytes of interest.

In some embodiments, a counter ion may be used to achieve the desired ionization state for MS analysis. For example, a counter ion may be used to change the polarity of the ionization of LGPC for MS analysis in negative ionization mode. Exemplary counter ions may include ammonium chloride, ammonium acetate, ammonium formate, ammonium bromide, ammonium sulfate, or ammonium nitrate. Additional, alternative counter ions may also be used.

In some embodiments, LGPC may be measured under positive multiple reaction monitoring (MRM) mode by implementing polarity switch on the MS instrument.

In some embodiments, the concentration of formic acid in mobile phase A may be between 0.001% and 0.1%.

DETAILED DESCRIPTION

Figure 1:
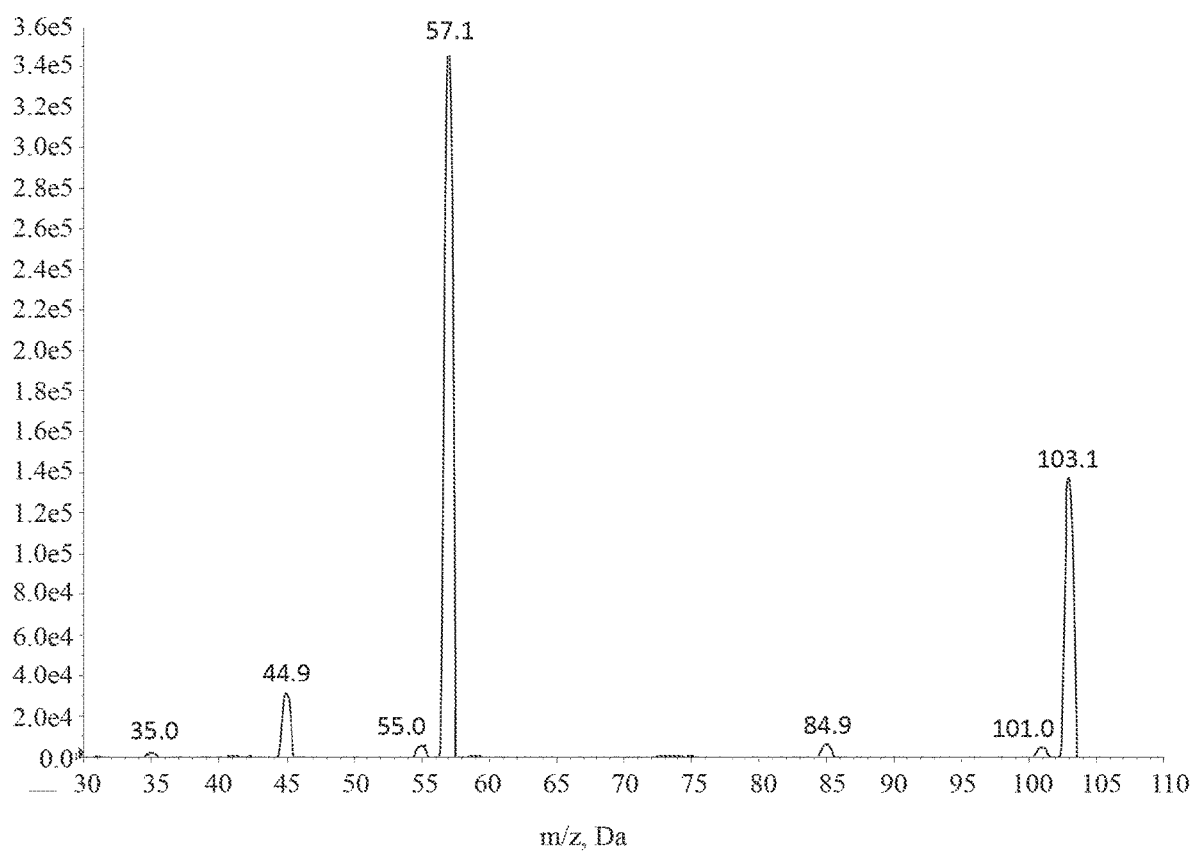
FIG. 1 shows exemplary parent and daughter ion peaks generated from tandem mass spectrometric fragmentation of 2-HB.

Methods are described for measuring the amount of one or more analytes selected from the group of metabolites consisting of: 2-hydroxybutyric acid (2-HB), 3-hydroxybutyric acid (3-HB), 4-methyl-2-oxopentanoic acid (4-MOP), 1-linoleoyl-2-hydroxy-sn-glycero-3-phosphocholine (LGPC), oleic acid (oleate), pantothenic acid (pantothenate, vitamin B5), and serine in a sample. Mass spectrometric methods are described for quantifying single and multiple analytes in a sample using a single injection method. The methods may use a liquid chromatography step such as UPLC to perform a separation (purification, enrichment) of selected analytes combined with methods of mass spectrometry, thereby providing a high-throughput assay system for quantifying a plurality of analytes in a sample that is amenable to automation.

The methods presented herein provide advantages over current methods to measure these analytes. The method uses a single injection to measure one or more and up to seven analytes. Further, the method uses a single injection to measure analytes having different ionization polarities. That is, analytes that are typically measured using negative ionization mode can be measured using positive ionization mode, and analytes that are typically measured using positive ionization mode can be measured using negative ionization mode. The ability to measure, in a single injection, a plurality of analytes in various combinations, including an embodiment to measure up to seven analytes, reduces the time required to obtain analysis results, uses fewer resources in terms of laboratory disposables (e.g., tubes, pipette tips, reagents), laboratory instruments and human resources. These improvements lead to savings by decreasing the costs of the assays and increasing the instrument and laboratory capacity for sample analysis.

Prior to describing this invention in further detail, the following terms are defined.

Definitions:

The term "solid phase extraction" refers to a sample preparation process where components of complex mixture (i.e., mobile phase) are separated according to their physical and chemical properties using solid particle chromatographic packing material (i.e. solid phase or stationary phase). The solid particle packing material may be contained in a cartridge type device (e.g. a column).

The term "separation" refers to the process of separating a complex mixture into its component molecules or metabolites. Common, exemplary laboratory separation techniques include electrophoresis and chromatography.

The term "chromatography" refers to a physical method of separation in which the components (i.e., chemical constituents) to be separated are distributed between two phases, one of which is stationary (stationary phase) while the other (the mobile phase) moves in a definite direction. The mobile phase may be gas ("gas chromatography", "GC") or liquid ("liquid chromatography", "LC"). Chromatographic output data may be used in embodiments of the method described herein.

The term "liquid chromatography" or "LC" refers to a process of selective inhibition of one or more components of a fluid solution as the fluid uniformly moves through a column of a finely divided substance or through capillary passageways. The inhibition results from the distribution of the components of the mixture between one or more stationary phases and the mobile phase(s) as the mobile phase (s) move relative to the stationary phase(s). Examples of "liquid chromatography" include "Reverse phase liquid chromatography" or "RPLC", "high performance liquid chromatography" or "HPLC", "ultra-high performance liquid chromatography" or "UPLC" or "UHPLC".

The term "retention time" refers to the elapsed time in a chromatography process since the introduction of the sample into the separation device. The retention time of a constituent of a sample refers to the elapsed time in a chromatography process between the time of injection of the sample into the separation device and the time that the constituent of the sample elutes (e.g., exits from) the portion of the separation device that contains the stationary phase.

The term "retention index" of a sample component refers to a number, obtained by interpolation (usually logarithmic), relating the retention time or the retention factor of the sample component to the retention times of standards eluted before and after the peak of the sample component, a mechanism that uses the separation characteristics of known standards to remove systematic error.

The term "separation index" refers to a metric associated with chemical constituents separated by a separation technique. For chromatographic separation techniques, the separation index may be retention time or retention index. For non-chromatographic separation techniques, the separation index may be physical distance traveled by the chemical constituent.

As used herein, the terms "separation information" and "separation data" refer to data that indicates the presence or absence of chemical constituents with respect to the separation index. For example, separation data may indicate the presence of a chemical constituent having a particular mass eluting at a particular time. The separation data may indicate that the amount of the chemical constituent eluting over time rises, peaks, and then falls. A graph of the presence of the chemical constituent plotted over the separation index (e.g., time) may display a graphical peak. Thus, within the context of separation data, the terms "peak information" and "peak data" are synonymous with the terms "separation information" and "separation data".

The term "Mass Spectrometry" (MS) refers to a technique for measuring and analyzing molecules that involves ionizing or ionizing and fragmenting a target molecule, then analyzing the ions, based on their mass/charge ratios, to produce a mass spectrum that serves as a "molecular fingerprint". Determining the mass/charge ratio of an object may be done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain identifications of target molecules.

The terms "operating in negative mode" or "operating in negative MRM mode" or "operating in negative ionization mode" refer to those mass spectrometry methods where negative ions are generated and detected. The terms "operating in positive mode" or "operating in positive MRM mode" or "operating in positive ionization mode" refer to those mass spectrometry methods where positive ions are generated and detected.

The term "mass analyzer" refers to a device in a mass spectrometer that separates a mixture of ions by their mass-to-charge ("m/z") ratios.

The term "m/z" refers to the dimensionless quantity formed by dividing the mass number of an ion by its charge number. It has long been called the "mass-to-charge" ratio.

As used herein, the term "source" refers to a device in a mass spectrometer that ionizes a sample to be analyzed. Examples of ion sources include electrospray ionization (ESI), atmospheric pressure chemical ionization (APCI), heated electrospray ionization (HESI), atmospheric pressure photoionization (APPI), flame ionization detector (FID), matrix-assisted laser desorption ionization (MALDI), etc.

As used herein, the term "detector" refers to a device in a mass spectrometer that detects ions.

The term "ion" refers to any object containing a charge, which can be formed for example by adding electrons to or removing electrons from the object.

The term "mass spectrum" refers to a plot of data produced by a mass spectrometer, typically containing m/z values on x-axis and intensity values on y-axis.

The term "scan" refers to a mass spectrum that is associated with a particular separation index. For example, systems that use a chromatographic separation technique may generate multiple scans, each scan at a different retention time.

The term "run time", refers to the time from sample injection to generation of the instrument data. The total run time includes chromatography and mass spectrometry for the sample.

The term "tandem MS" refers to an operation in which a first MS step, called the "primary MS", is performed, followed by performance of one or more of a subsequent MS step, generically referred to as "secondary MS". In the primary MS, an ion, representing one (and possibly more than one) chemical constituent, is detected and recorded during the creation of the primary mass spectrum. The substance represented by the ion is subjected to a secondary MS, in which the substance of interest undergoes fragmentation in order to cause the substance to break into subcomponents, which are detected and recorded as a secondary mass spectrum. In a true tandem MS, there is an unambiguous relationship between the ion of interest in the primary MS and the resulting peaks created during the secondary MS. The ion of interest in the primary MS corresponds to a "parent" or precursor ion, while the ions created during the secondary MS correspond to sub-components of the parent ion and are herein referred to as "daughter" or "product" ions.

Thus, tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion. Tandem MS may be repeated on daughter ions to determine "grand-daughter" ions, for example. Thus, tandem MS is not limited to two-levels of fragmentation, but is used generically to refer to multi-level MS, also referred to as "$MS^{11}$". The term "MS/MS" is a synonym for "$MS^2$". For simplicity, the term "daughter ion" hereinafter refers to any ion created by a secondary or higher-order (i.e., not the primary) MS.

The "level" of one or more biomarkers means the absolute or relative amount or concentration of the biomarker measured in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological fluid or tissue such as, for example, blood, blood plasma (plasma), blood serum (serum), urine, cerebral spinal fluid (CSF), or tissue.

"Subject" means any animal, but is preferably a mammal, such as, for example, a human, monkey, mouse, rabbit or rat.

I. Sample Preparation and Quality Control (QC)

Sample extracts containing analytes are prepared by isolating the analytes away from the macromolecules (e.g., proteins, nucleic acids, lipids) that may be present in the sample. Some or all analytes in a sample may be bound to proteins. Various methods may be used to disrupt the interaction between analyte(s) and protein prior to MS analysis. For example, the analytes may be extracted from a sample to produce a liquid extract, while the proteins that may be present are precipitated and removed. Proteins may be precipitated using, for example, a solution of ethyl acetate or methanol. To precipitate the proteins in the sample, an ethyl acetate or methanol solution is added to the sample, then the mixture may be spun in a centrifuge to separate the liquid supernatant, which contains the extracted analytes, from the precipitated proteins In other embodiments, analytes may be released from protein without precipitating the protein. For example, a formic acid solution may be added to the sample to disrupt the interaction between protein and analyte. Alternatively, ammonium sulfate, a solution of formic acid in ethanol, or a solution of formic acid in methanol may be added to the sample to disrupt ionic interactions between protein and analyte without precipitating the protein.

In some embodiments the extract may be subjected to various methods including liquid chromatography, electrophoresis, filtration, centrifugation, and affinity separation as described herein to purify or enrich the amount of the selected analyte relative to one or more other components in the sample.

To assess, for example, precision, accuracy, calibration range, or analytical sensitivity of methods of detecting and quantifying analytes, quality control (QC) samples may be used. The concentration of a given analyte(s) to be used in a QC sample may be determined based on lower limit of quantitation (LLOQ) or upper limit of quantitation (ULOQ) of the given analyte(s), as detected in a sample. In one example, the LLOQ may be represented by the concentration of a standard (e.g., Standard A), and the ULOQ may be represented by the concentration of a second standard (e.g., Standard H). The Low QC value may be set at a concentration of about 3×LLOQ, the Mid QC value may be at a concentration of about 25-50% of High QC, and the High QC value may be at a concentration of about 80% of the ULOQ. The QC target concentration levels may be chosen based on a combination of the Analytical Measurement Range (AMR) and the frequency of sample results as measured in a set of representative samples.

II. Chromatography

Prior to mass spectrometry, the analyte extract may be subjected to one or more separation methods such as electrophoresis, filtration, centrifugation, affinity separation, or chromatography. In one embodiment the separation method may comprise liquid chromatography (LC), including, for example, ultra high performance LC (UHPLC).

In some embodiments, UHPLC may be conducted using a reversed phase column chromatographic system, hydrophilic interaction chromatography (HILIC), or a mixed phase column chromatographic system.

The column heater for LC may be set at a temperature of from about 25° C. to about 80° C. For example, the column heater may be set at about 40° C., 50° C., 60° C., 70° C., etc.

In an example, UHPLC may be conducted using a reversed phase column chromatographic system. The system may comprise two or more mobile phases. Mobile phases may be referred to as, for example, mobile phase A, mobile phase B, mobile phase A', and mobile phase B'.

In an exemplary embodiment using two mobile phases, A and B, mobile phase A may comprise formic acid, water, and $NH_4Cl$, and mobile phase B may comprise methanol, acetonitrile, and $NH_4Cl$. The concentration of formic acid in mobile phase A may range from 0.001% to 0.1%. Further, the composition of mobile phase A may range from 0.01:1000:0.001 to 1.0:1000:0.01 (formic acid:water:$NH_4Cl$, v/v/wt). In an exemplary embodiment, mobile phase A may be prepared at a volume/volume/weight (v/v/wt) ratio of 0.025:1000:0.001. In further embodiments, mobile phase B may be prepared at a v/v/wt ratio of 2000:1000:0.001.

In one example, linear gradient elution may be used for chromatography. The starting conditions for linear gradient elution may include the concentration of a mobile phase (e.g., mobile phase B) and/or the flow rate of a mobile phase through the column (e.g., mobile phase B). The starting conditions may be optimized for the separation and/or retention of one or more analytes. For example, the starting conditions for the gradient may be optimized for the separation of 3-MOP and 4-MOP by starting with no more than 5% of mobile phase B and a flow rate ranging from 300 to 800 µL/min. In another example, the starting conditions for the gradient may also be optimized for the retention of 2-HB and 3-HB on the column by starting with no more than 5% of mobile phase B. The gradient conditions may also be optimized for the separation and/or retention of analytes and may vary depending on the flow rate selected. For example, with initial conditions of 5% mobile phase B and 650 µL/min flow rate, mobile phase B may be increased to 40% in 0.8 min and then to 99% in 0.01 min and maintained for 1.09 min. Mobile phase B may revert to 5% in 0.01 min for equilibration for next sample injection. The flow rate may be changed from 650 to 800 µL/min from 1.50 to 1.55 min and then back to 650 µL/min from 2.20 to 2.21 min.

In other embodiments, mobile phase A may comprise perfluoropentanoic acid (PFPA) and water, and mobile phase B may comprise PFPA and acetonitrile. The concentration of PFPA may be from about 0.01 to about 0.500%. For example, the concentration of PFPA may be about 0.05%. In a further example, mobile phase A may be 0.05% perfluoropentanoic acid (PFPA) in water, and mobile phase B may be 0.05% PFPA in acetonitrile. Linear gradient elution may be used for chromatography and may be carried out with an initial condition of 1% mobile phase B held for 0.5 min. The proportion of mobile phase B may then be increased to 39% in 1.1 min. The proportion of mobile phase B may be increased to 80% in 0.2 min and then back to 1% in 0.1 min for equilibration for the next injection. The flow rate may be set at 800 µL/min and the total run time may be less than 3 minutes.

In yet other embodiments, mobile phase A may comprise formic acid and water, and mobile phase B may comprise acetonitrile and methanol. In an exemplary embodiment, mobile phase A may contain from about 0.001 to about 0.100% formic acid, and mobile phase B may contain any amount of acetonitrile from 0-100%. In an example, the concentration of mobile phase A may be about 0.0100% formic acid in water and the concentration of mobile phase B may be about 50% acetonitrile in methanol. Linear gradient elution may be used for chromatography and may be carried out with initial conditions of 1% mobile phase B and a flow rate was 800 µL/min. Mobile phase B may be maintained at 1% at 0.5 min, increased to 16% at 2.50 min, to 46% at 3.50 min, and may then be decreased to 1.0% at 3.60 min and at 4.50 min.

III. Mass Spectrometry and Quantitation

One or more analytes may be ionized by any method known to the skilled artisan, including, for example, mass spectrometry. Mass spectrometry is performed using a mass spectrometer that includes an ion source for ionizing the fractionated sample and creating charged molecules for further analysis. Ionization of the sample may be performed by, for example, electrospray ionization (ESI). Other ion sources may include, for example, atmospheric pressure chemical ionization (APCI), heated electrospray ionization (HESI), atmospheric pressure photoionization (APPI), flame ionization detector (FID), or matrix-assisted laser desorption ionization (MALDI). The choice of ionization method may be determined based on a number of considerations. Exemplary considerations include the analyte to be measured, type of sample, type of detector, and the choice of positive or negative mode.

The one or more analytes may be ionized in positive or negative mode to create one or more ions. For example, the analytes 2-HB, 3-HB, 4-MOP, serine, pantothenate, oleic acid, and LGPC may be ionized in negative mode. The analytes ionized in negative mode may be analyzed in a single sample injection. In another example, the analytes serine, pantothenate, and LGPC may be ionized in positive mode. In some embodiments, the analytes ionized in positive mode may be analyzed in one sample injection, and the analytes ionized in negative mode may be analyzed in a separate sample injection. In another embodiment, the analytes ionized in positive mode and the analytes ionized in negative mode may be analyzed in a single sample injection.

Mass spectrometer instrument settings may be optimized for the given method and/or for the particular mass spectrometer used. The instrument may use various gases, for example, nitrogen, helium, argon, or zero air. In one example, mass spectrometry may be performed using AB Sciex QTrap 5500 mass spectrometers. The instrument may be operated in negative multiple reaction monitoring (MRM) mode. Ionspray voltage settings may range from −4 kV to −5 kV; in one embodiment the voltage may be set at −4.5 kV. The source temperature may range from about 500° C. to 600° C.; in one embodiment the source temperature may be set at 550° C. The curtain gas may range from 20 to 40 or another appropriate value; in one embodiment the curtain gas may be set at 30. The nebulizer and desolvation gas flow rates may range from 60 to 80 or another appropriate value; in one embodiment the flow rates may be set at 70. The collisionally activated dissociation (CAD) gas may range from high to low. In one embodiment the CAD may be set, for example, at low. Further exemplary MS settings are described in Table 1.

In another example, the mass spectrometer may be operated in positive MRM mode. The ionspray voltage setting may range from 2.5 kV to 3.5 kV; in one embodiment the voltage may be set at 3.0 kV. The source temperature may range from about 500° C. to 600° C.; in one embodiment the source temperature may be set at 550° C. The curtain gas may range from 10 to 30 or another appropriate value; in one embodiment the curtain gas is set at 20. The nebulizer and desolvation gas flow rates may range from 60 to 80 or another appropriate value; in one embodiment the flow rates are set may be set at 70. The CAD gas setting may range from high to low; in one embodiment the CAD gas is set at high. Declustering potential may range from less than 40V to more than 45V. In one embodiment the declustering potential may be set at 41V. The collision energy may range from less than 45 eV to more than 45 eV. In one embodiment the collision energy is set at 45 eV. The entrance potential setting may range from less than about 10V to more than 10V; in an embodiment the entrance potential is set at 10 V. The collision cell exit potential setting may range from less than 8V to more than 8V; in an embodiment the collision exit potential is set at 8 V.

After a sample has been ionized, the positively or negatively charged ions may be analyzed to determine a mass-to-charge ratio. Exemplary suitable analyzers for determining mass-to-charge ratios include quadrupole analyzers, ion trap analyzers, and time of flight analyzers. The ions may be detected using, for example, a selective mode or a scanning mode. Exemplary scanning modes include multiple reaction monitoring (MRM) and selected reaction monitoring (SRM).

Analysis results may include data produced by tandem MS. In exemplary embodiments, tandem MS may be accurate-mass tandem MS. For example, the accurate-mass tandem mass spectrometry may use a quadrupole time-of-flight (Q-TOF) analyzer. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

For example, a primary mass spectrum may contain five distinct ions, which may be represented as five graphical peaks. Each ion in the primary MS may be a parent ion. Each parent ion may be subjected to a secondary MS that produces a mass spectrum showing the child ions for that particular parent ion.

The parent/daughter relationship may be extended to describe the relationship between separated components (e.g., components eluting from the chromatography state)

and ions detected in the primary MS, and to the relationship between the sample to be analyzed and the separated components.

The mass spectrometer typically provides the user with an ion scan (i.e., a relative abundance of each ion with a particular mass/charge over a given range). Mass spectrometry data may be related to the amount of the analyte in the original sample by a number of methods. In one example, a calibration standard is used to generate a standard curve (calibration curve) so that the relative abundance of a given ion may be converted into an absolute amount of the original analyte. In another example, the calibration standard may be an external standard and a standard curve may be generated based on ions generated from those standards to calculate the quantity of one more analytes. In a further example, the external standard may be an unlabeled analyte.

Internal standards may be added to calibration standards and/or test samples. An internal standard may be used to account for loss of analytes during sample processing in order to get a more accurate value of a measured analyte in the sample. The ratio of analyte peak area to internal standard peak area in the levels of the calibration standards may be used to generate a calibration curve and quantitate samples. One or more isotopically labeled analogs of analytes for example, 2-HB-$d_3$, 3-HB-$d_4$, 4-MOP-$d_3$, serine-$d_3$, pantothenate-$^{13}C_3$-$^{15}N$, oleic acid-$^{13}C_{18}$, and LGPC-$d_9$ may be used as internal standards. Other suitable internal standards include, for example, sodium D-3-HB-$^{13}C_4$, sodium D-3-HB-2,4-$^{13}C_2$ sodium D-3-HB-4,4,4-$d_3$, sodium(+/−)-3-HB-2,2-$d_2$, sodium (+/−)-3-HB-2,4-$^{13}C_2$, L-serine-$^{13}C_3$-$d_3$-$^{15}N$, DL-serine-$^{13}C_3$-$^{15}N$, L-serine-$^{13}C_3$, L-serine-$^{13}C_3$-$^{15}N$, DL-serine-2,3,3-$d_3$, L-serine-2,3,3-$d_3$-$^{15}N$, DL-serine-3,3-$d_2$, L-serine-3,3-$d_2$, L-serine-$d_7$, oleic acid-11,11-$d_2$ oleic acid-9,10-$d_2$ and oleic acid-$d_{33}$.

The analysis data may be sent to a computer and processed using computer software. In one example, peak area ratios of analyte to internal standard are fitted against the concentrations of the calibration standards using a statistical regression method for quantitation. In another example, the statistical regression is weighted linear least squares regression. The slope and intercept calculated using the calibration curve may be used to calculate the unknown concentrations of analytes in experimental samples.

IV. Kit

A kit for assaying one or more of the analytes selected from the group consisting of 2-HB, 3-HB, 4-MOP, serine, pantothenate, oleic acid, and LGPC may comprise the compositions and methods described herein. For example, a kit may include packaging material and measured amounts of one or more internal standards in amounts sufficient for one or more assays. In exemplary embodiments, the internal standards may be isotopically labeled, the kit may comprise pre-made mobile phase solutions, and/or the kit may comprise mobile phase reagents and instructions to prepare the mobile phase solutions. Kits may also comprise instructions recorded in tangible form (e.g. on paper such as, for example, an instruction booklet or an electronic medium) for using the reagents to measure the one or more analytes.

EXAMPLES

I. General Methods

A. Reagents and Instruments

Mass spectrometric grade (98%) formic acid and ammonium chloride (99.5%) were obtained from Sigma-Aldrich; HPLC grade methanol and water were obtained from Fisher Scientific; and HPLC grade acetonitrile and ethanol were obtained from Acros. A Multi-Tube Vortexer from VWR Scientific was used for mixing. Centrifugation of plates was carried out in a Sorvall ST 40R centrifuge from Thermo Scientific with a 3617 bucket rotor. Human plasma (K2-EDTA) was obtained from Bioreclamation. Intralipid, bilirubin, bovine serum albumin (fatty acid free) and perfluoropentanoic acid (PFPA) were obtained from Sigma-Aldrich. L-Serine, (S)-2-hydroxybutyric acid, sodium (±)-3-hydroxybutyrate, 4-methyl-2-oxopentanoic acid, oleic acid, and oleic acid-$^{13}C_{18}$ were purchased from Sigma-Aldrich; calcium D-pantothenate was obtained from MP Biochemicals; 1-linoleoyl-2-hydroxy-sn-glycero-3-phosphocholine and 1-linoleoyl-2-hydroxy-sn-glycero-3-phosphocholine-N,N,N-trimethyl-$d_9$ was obtained from Avanti Polar Lipids; L-serine-2,3,3-$d_3$ and calcium pantothenate (β-alanine-$^{13}C_3$, $^{15}N$) was obtained from Cambridge Isotope Laboratories; sodium (±)-2-hydroxybutyrate-2,3,3-$d_3$, sodium (±)-3-hydroxybutyrate-3,4,4,4-$d_4$, and sodium 4-methyl-$d_3$-2-oxopentanoate was obtained from CDN Isotopes.

B. Sample Preparation

Sample preparation was carried out in a polypropylene 96-well plate. For calibration standards, blanks, and blanks with internal standard samples, 50 μL of water was transferred to the appropriate wells. For QC and study samples, 50 μL of plasma (thawed on ice) was transferred to the appropriate wells. For calibration standards, 40 μL of the corresponding calibration spiking solutions was added. All other samples were combined with 40 μL of acetonitrile/water/ethanol mixture (1:1:2). A 20 μL aliquot of working internal standard (WIS) solution was added to each well except for blanks, to which was added 20 μL of acetonitrile/water/ethanol mixture (1:1:2). The WIS solution may be comprised of one or more internal standards and may comprise one or more internal standards for each of the seven analytes described herein. Metabolite extraction was performed by adding a solution of 1% formic acid in methanol (200 μL) to each well. The plate was capped, vortexed for 2 minutes at room temperature, and centrifuged for 5 minutes at 3000 rpm at 4° C. An aliquot of 150 μL of the supernatant was transferred to a new plate for LC-MS/MS analysis. To assess sample recovery, QC samples were spiked with a concentration equivalent to calibration standard D, which represents the mid QC value for the given analyte. The calibration standards for each analyte are presented below in Table 3 of Example 1; the calibration values for standard D are presented in the column headed "D". Stock solutions, calibration spiking solutions, and internal standard solutions were stored at 4° C.

For 2-HB, the QC samples were spiked with a concentration of 5.00 μg/mL 2-HB, which was equivalent to calibration standard D.

For 3-HB, the QC samples were spiked with a concentration of 10.00 μg/mL 3-HB, which was equivalent to calibration standard D.

For 4-MOP, the QC samples were spiked with a concentration of 5.00 μg/mL 4-MOP, which was equivalent to calibration standard D.

For serine, the QC samples were spiked with a concentration of 25.0 μg/mL serine, which was equivalent to calibration standard D.

For pantothenate, the QC samples were spiked with a concentration of 0.100 μg/mL pantothenate, which was equivalent to calibration standard D.

For oleic acid, the QC samples were spiked with a concentration of 100 μg/mL oleic acid, which was equivalent to calibration standard D.

For LGPC, the QC samples were spiked with a concentration of 25.00 μg/mL LGPC, which was equivalent to calibration standard D.

A WIS solution for 2-HB-d$_3$ was prepared in acetonitrile/water/ethanol (1:1:2) at a concentration of 40.0 μg/mL.

A WIS solution for 3-HB-d$_4$ was prepared in acetonitrile/water/ethanol (1:1:2) at a concentration of 30.0 μg/mL.

A WIS solution for 4-MOP-d$_3$ was prepared in acetonitrile/water/ethanol (1:1:2) at a concentration of 20.0 μg/mL.

A WIS solution for serine-d$_3$ was prepared in acetonitrile/water/ethanol (1:1:2) at a concentration of 50.0 μg/mL.

A WIS solution for pantothenate-$^{13}C_3$, $^{15}N$ was prepared in acetonitrile/water/ethanol (1:1:2) at a concentration of 0.700 μg/mL.

A WIS solution for oleic acid-$^{13}C_{18}$ was prepared in acetonitrile/water/ethanol (1:1:2) at a concentration of 20.0 μg/mL.

A WIS solution for LGPC-d$_9$ was prepared in acetonitrile/water/ethanol (1:1:2) at a concentration of 20.0 μg/mL.

C. Chromatography

Agilent 1290 Infinity UHPLC systems, each equipped with a binary solvent pump unit, a refrigerated autosampler (set at 4° C.), and a column heater (set at 50° C., unless otherwise indicated) were used for liquid chromatography with a reversed phase column (Waters ACQUITY UPLC® BEH C18, 1.7 μm, 2.1×100 mm). Mobile phase A was formic acid/water/NH$_4$Cl (0.025:1000:0.001, v/v/wt) and mobile phase B was methanol/acetonitrile/NH$_4$Cl (2000:1000:0.001, v/v/wt), unless otherwise indicated. Linear gradient elution, was carried out with an initial condition of 5% mobile phase B (95% mobile phase A) and 650 μL/min flow rate unless otherwise indicated. Mobile phase B was increased from the initial 5% to 40% (60% mobile phase A) in 0.8 min and then from 40% to 99% (1% mobile phase A) in 0.01 min and maintained for 1.09 min. Then, mobile phase B reverted to 5% (95% mobile phase A) in 0.01 min for equilibration before the next sample was injected. The flow rate was increased from 650 μL/min to 800 μL/min from 1.50 to 1.55 min and then decreased back to 650 μL/min from 2.20 to 2.21 min. The run time was 2.21 min. A single fixed aliquot of 0.5-1.0 μL of the final extraction solution was injected onto the chromatography column for each sample analyzed. The eluent from the chromatography column was directly and automatically introduced into the electrospray source of a mass spectrometer. Isopropanol was used for needle wash unless otherwise indicated.

Example 1: LC-MS/MS Measurement of Analytes

Reversed phase liquid chromatography was performed on extracted samples as described above in the description of Chromatography in the General Methods section.

Mass spectrometry was performed on the samples using AB Sciex QTrap 5500 mass spectrometers. The instruments were operated in negative multiple reaction monitoring (MRM) mode. Ionspray voltage was set at −4.5 kV, source temperature at 550° C., curtain gas (e.g., nitrogen) at 30, and nebulizer and desolvation gas (e.g., nitrogen) flow rates at 70, collisionally activated dissociation (CAD) gas (e.g., nitrogen) at low. The detailed MS setting for each analyte is described in Table 1.

TABLE 1

Mass Spectrometer Method Settings

| Analyte | Dwell Time (msec) | DP (V) | EP (V) | CE (eV) | CXP (V) |
|---|---|---|---|---|---|
| 2-HB | 18 | −55 | −10 | −8 | −9 |
| 2-HB-d$_3$ | 18 | −55 | −10 | −7 | −9 |
| 3-HB | 18 | −35 | −10 | −6 | −9 |
| 3-HB-d$_4$ | 18 | −35 | −10 | −8 | −9 |
| 4-MOP | 36 | −30 | −10 | −10.5 | −7.5 |
| 4-MOP-d$_3$ | 18 | −30 | −10 | −12 | −9 |
| Serine | 18 | −60 | −10 | −20 | −15 |
| Serine-d$_3$ | 18 | −60 | −10 | −20 | −15 |
| Pantothenate | 18 | −90 | −10 | −18 | −15 |
| Pantothenate-$^{13}C_3$—$^{15}N$ | 18 | −90 | −10 | −18 | −15 |
| Oleic acid | 18 | −100 | −10 | −40 | −5 |
| Oleic acid-$^{13}C_{18}$ | 18 | −100 | −10 | −30 | −5 |
| LGPC | 18 | −100 | −10 | −70 | −5 |
| LGPC-d$_9$ | 18 | −100 | −10 | −70 | −5 |

Raw data were acquired from the instrument and processed using Analyst 1.6.2 software (AB Sciex). For quantitation, peak area ratios of analyte to internal standard were fitted against the concentrations of the calibration standards by weighted (1/x$^2$) linear least squares regression. The resulting slope and intercept of the calibration curve were used to calculate the unknown concentrations in experimental samples. The parent and daughter ions used in this example for quantitation of each analyte are listed in Table 2 under the columns headed "Parent ion (m/z)" and "Daughter ion for quantitation (m/z)", respectively. With the exception of oleic acid, the most intense daughter ion for each analyte was selected to use for quantitation. For oleic acid, none of the daughter ions had sufficient sensitivity to encompass the calibration range.

TABLE 2

Parent and Daughter Ion Mass to Charge Ratios of Analytes as measured in negative ionization mode

| Analyte | Parent ion (m/z) | Daughter ion for quantitation (m/z) | Additional daughter ions (m/z) |
|---|---|---|---|
| 2-HB | 103.1 ± 0.5 | 57.1 ± 0.5 | 35.0 ± 0.5, 44.9 ± 0.5, 55.0 ± 0.5, 84.9 ± 0.5, 101.0 ± 0.5 |
| 2-HB-d$_3$ | 106.1 ± 0.5 | 59.1 ± 0.5 | |
| 3-HB | 103.1 ± 0.5 | 59.1 ± 0.5 | 41.1 ± 0.5 |
| 3-HB-d$_4$ | 107.1 ± 0.5 | 59.1 ± 0.5 | |
| 4-MOP | 129.0 ± 0.5 | 85.1 ± 0.5 | None |
| 4-MOP-d$_3$ | 132.1 ± 0.5 | 88.1 ± 0.5 | |
| Serine | 104.0 ± 0.5 | 74.0 ± 0.5 | 40.1 ± 0.5, 42.0 ± 0.5, 45.0 ± 0.5, 56.0 ± 0.5, 58.1 ± 0.5 |
| Serine-d$_3$ | 107.0 ± 0.5 | 75.0 ± 0.5 | |
| Pantothenate | 218.1 ± 0.5 | 88.0 ± 0.5 | 42.0 ± 0.5, 44.0 ± 0.5, 45.1 ± 0.5, 59.0 ± 0.5, 71.0 ± 0.5, 72.0 ± 0.5, 98.1 ± 0.5, 98.9 ± 0.5, 100.9 ± 0.5, 116.0 ± 0.5, 129.1 ± 0.5, 146.0 ± 0.5 |
| Pantothenate-$^{13}C_3$—$^{15}N$ | 222.1 ± 0.5 | 92.0 ± 0.5 | |
| Oleic acid | 281.3 ± 0.5 | N/A | 44.7 ± 0.5, 61.8 ± 0.5, 79.8 ± 0.5, 143.1 ± 0.5, 183.0 ± 0.5, 194.9 ± 0.5, 206.9 ± 0.5, 209.0 ± 0.5, 210.1 ± 0.5, 223.1 ± 0.5, 237.1 ± 0.5, 251.1 ± 0.5 |

TABLE 2-continued

Parent and Daughter Ion Mass to Charge Ratios of Analytes as measured in negative ionization mode

| Analyte | Parent ion (m/z) | Daughter ion for quantitation (m/z) | Additional daughter ions (m/z) |
|---|---|---|---|
| Oleic acid-$^{13}C_{18}$ | 299.3 ± 0.5 | N/A | |
| LGPC | 554.3 ± 0.5 | 279.2 ± 0.5 | 34.9 ± 0.5, 79.0 ± 0.5, 153.0 ± 0.5, 167.9 ± 0.5, 224.1 ± 0.5, 242.0 ± 0.5, 504.4 ± 0.5 |
| LGPC-$d_9$ | 563.3 ± 0.5 | 279.2 ± 0.5 | |

The calibration range of each analyte was determined. For each analyte, the LLOQ represents the low end of the calibration range, and the high end of the calibration range is represented by the ULOQ. Eight calibrators (standards A-H) were used to cover the calibration ranges. The final analyte concentrations in each calibrator are listed in Table 3. Calibration spiking solutions were prepared in acetonitrile/water/ethanol (1:1:2) at 1.25 fold of the corresponding calibration concentrations.

TABLE 3

Calibration Ranges for Analytes

Actual Concentration of Calibration Range in Assay (µg/mL)

| Analyte | A | B | C | D | E | F | G | H |
|---|---|---|---|---|---|---|---|---|
| 2-HB | 0.500 | 1.00 | 2.50 | 5.00 | 10.0 | 20.0 | 36.0 | 40.0 |
| LGPC | 2.50 | 5.00 | 12.5 | 25.0 | 40.0 | 70.0 | 90.0 | 100 |
| Oleic Acid | 10.0 | 20.0 | 50.0 | 100 | 160 | 280 | 360 | 400 |
| 4-MOP | 0.500 | 1.00 | 2.50 | 5.00 | 8.00 | 14.0 | 18.0 | 20.0 |
| 3-HB | 1.00 | 2.00 | 5.00 | 10.0 | 20.0 | 40.0 | 72.0 | 80.0 |
| Serine | 2.50 | 5.00 | 12.5 | 25.0 | 40.0 | 70.0 | 90.0 | 100 |
| Pantothenate | 0.0100 | 0.0200 | 0.0500 | 0.100 | 0.200 | 0.400 | 0.720 | 0.800 |

QC levels were determined based on LLOQ and ULOQ. Low, mid, and high level QC samples were prepared from combination of human plasma pools of appropriate analyte concentrations with fortification of analytes as necessary. LLOQ samples were prepared in a fatty-acid free BSA solution (50 mg/mL in PBS) at the same concentrations as standard A in Table 3 for all analytes. QC samples were stored at −80° C.

FIGS. 1-7 show mass spectra resulting from fragmentation of the parent ions indicated in Table 2.

MRM transitions that were monitored for the quantitation of 2-HB in negative ionization mode include those produced by fragmenting a parent ion having a m/z of about 103.1±0.5 to produce daughter ions having m/z of about 57.1±0.5, 5.0±0.5, 44.9±0.5, 55.0±0.5, 84.9±0.5, and 101.0±0.5. These parent and daughter ion peaks generated from tandem mass spectrometric fragmentation of 2-HB are illustrated in FIG. 1. In this example, the daughter ion used for quantitation of 2-HB has m/z of about 57.1±0.5. The calibration range for 2-HB was determined to be 0.500 to 40.0 µg/mL.

Figure 2:
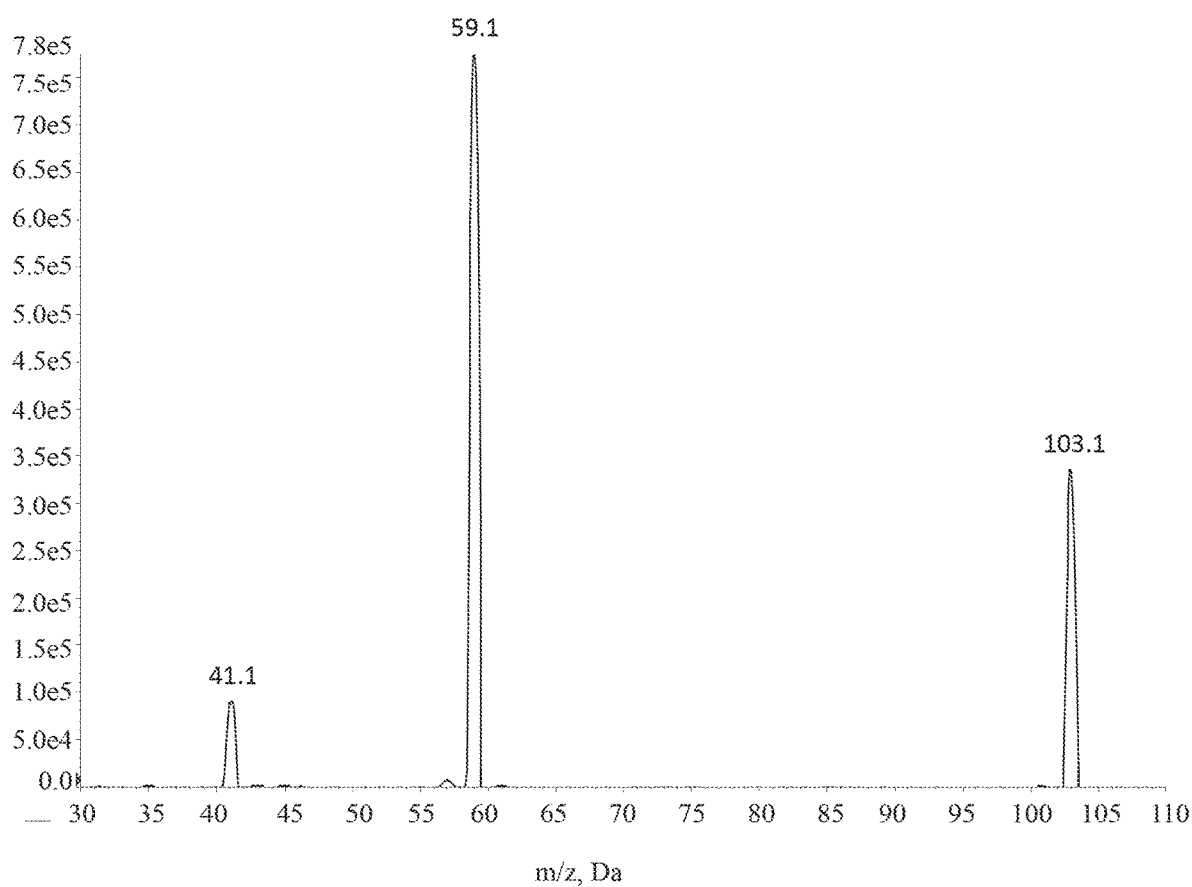
FIG. 2 shows exemplary parent and daughter ion peaks generated from tandem mass spectrometric fragmentation of 3-HB.

MRM transitions that were monitored for the quantitation of 3-HB in negative ionization mode include those produced by fragmenting a parent ion having m/z of about 103.1±0.5 to produce daughter ions having m/z of about 59.1±0.5 and 41.1±0.5. These parent and daughter ion peaks generated from tandem mass spectrometric fragmentation of 3-HB are illustrated in FIG. 2. In this example, the daughter ion used for quantitation of 3-HB has m/z of about 59.1±0.5. The calibration range for 3-HB was determined to be 1.00 to 80.0 µg/mL.

Figure 3:
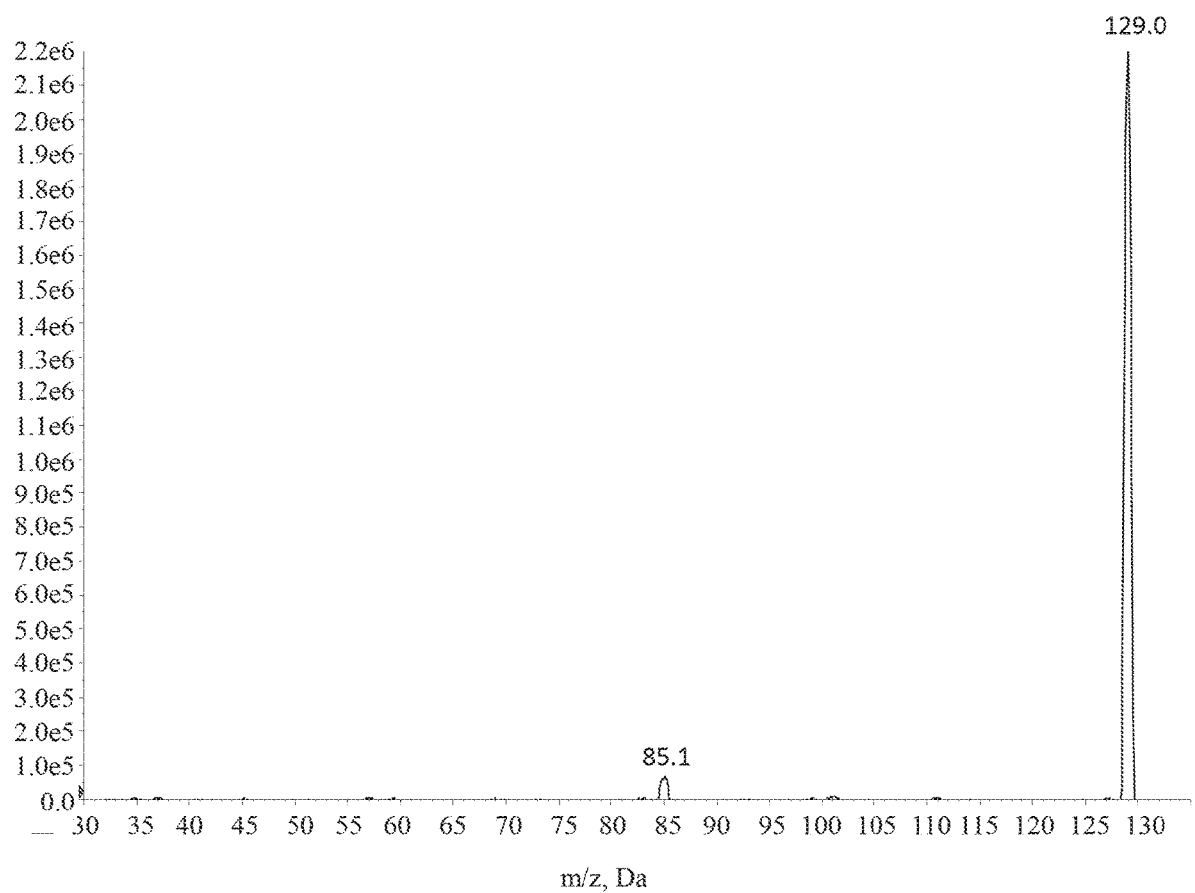
FIG. 3 shows exemplary parent and daughter ion peaks generated from tandem mass spectrometric fragmentation of 4-MOP.

MRM transitions that were monitored for the quantitation of 4-MOP in negative ionization mode include those produced by fragmenting a parent ion having m/z of about 129.0±0.5 to a daughter ion having a m/z of about 85.1±0.5. These parent and daughter ion peaks generated from tandem mass spectrometric fragmentation of 4-MOP are illustrated in FIG. 3. In this example, the daughter ion used for quantitation of 4-MOP has a m/z of about 85.1±0.5. The calibration range for 4-MOP was determined to be 0.500 to 20.0 µg/mL.

Figure 4:
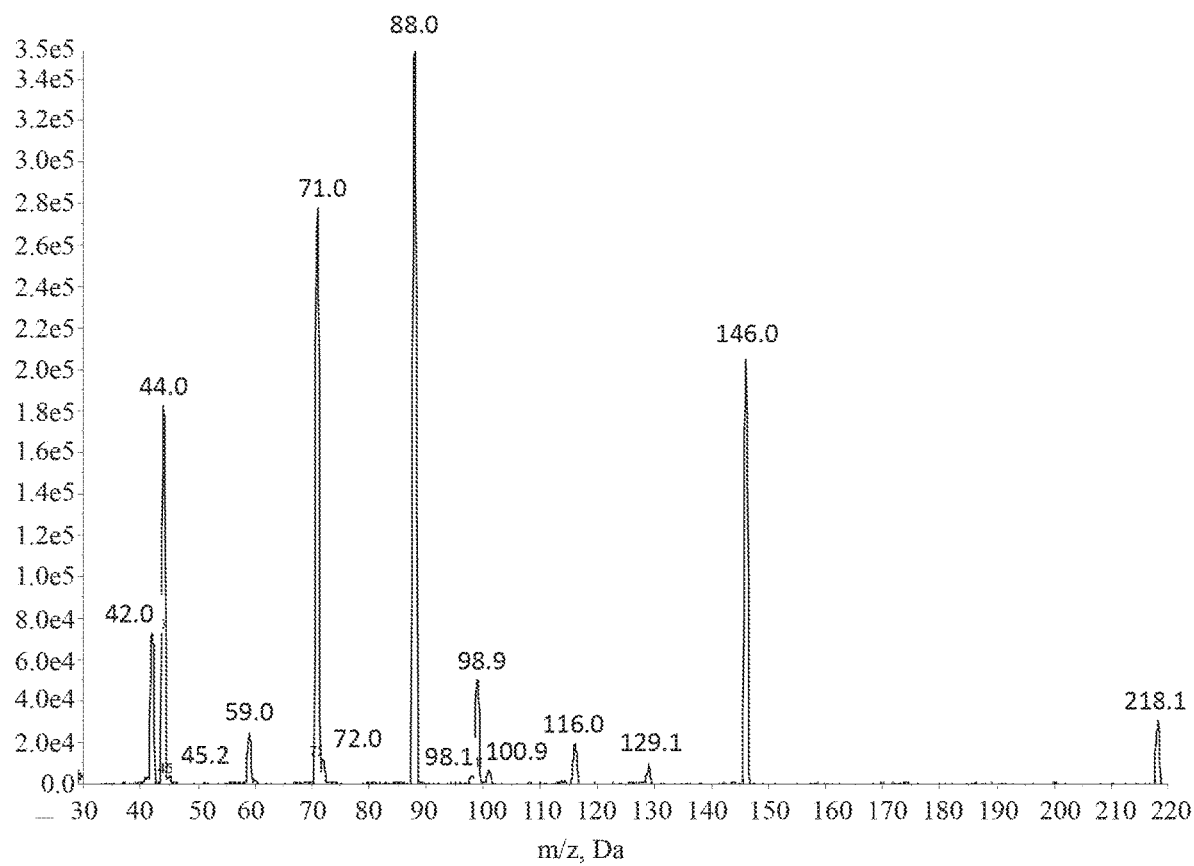
FIG. 4 shows exemplary parent and daughter ion peaks generated from tandem mass spectrometric fragmentation of pantothenate.

MRM transitions that were monitored for the quantitation of pantothenate in negative ionization mode include those produced by fragmenting a parent ion having a m/z of about 218.1±0.5 to produce daughter ions having m/z of about 88.0±0.5, 42.0±0.5, 44.0±0.5, 45.1±0.5, 59.0±0.5, 71.0±0.5, 72.0±0.5, 98.1±0.5, 98.9±0.5, 100.9±0.5, 116.0±0.5, 129.1±0.5, and 146.0±0.5. These parent and daughter ion peaks generated from tandem mass spectrometric fragmentation of pantothenate are illustrated in FIG. 4. In this example, the daughter ion used for quantitation of pantothenate has a m/z of about 88.0±0.5. The calibration range for pantothenate was determined to be 0.0100 to 0.800 µg/mL.

Figure 5:
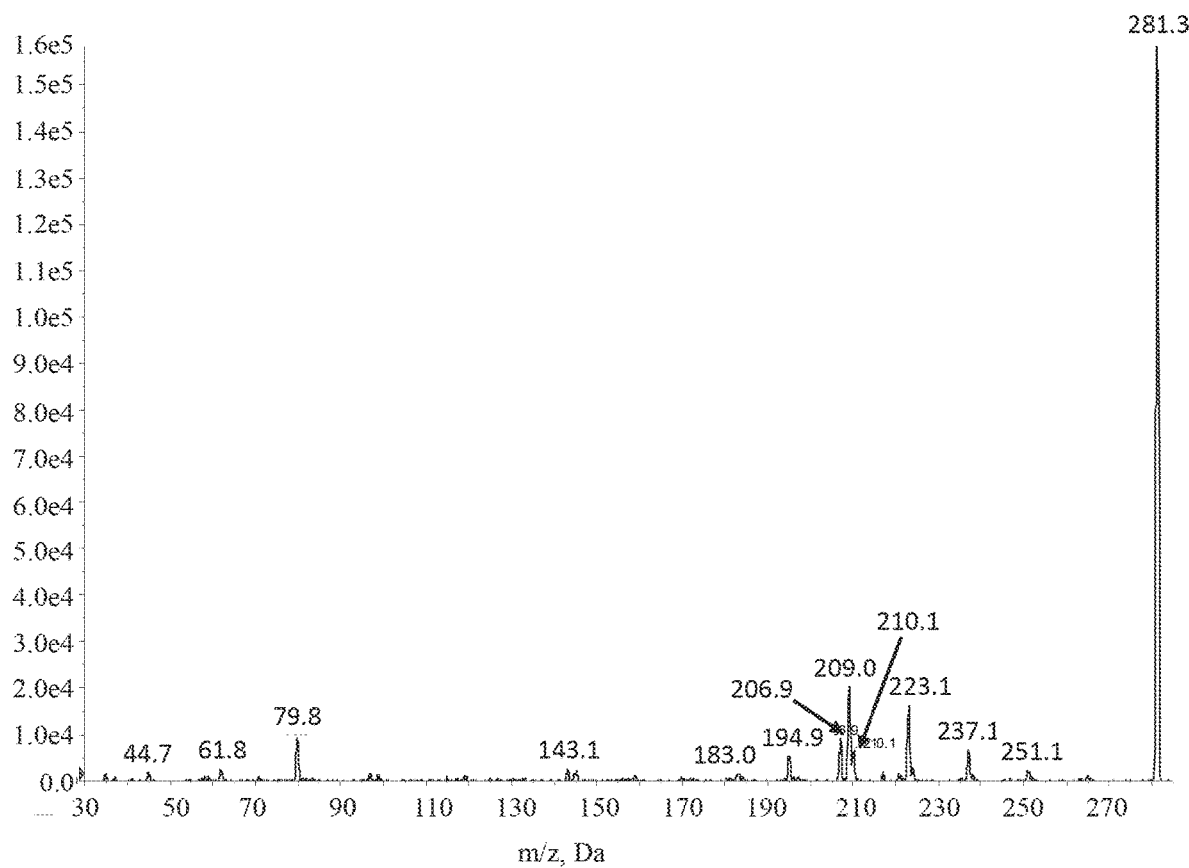
FIG. 5 shows exemplary parent and daughter ion peaks generated from tandem mass spectrometric fragmentation of oleic acid.

MRM transitions that were monitored for the quantitation of oleic acid in negative ionization mode include those produced by fragmenting a parent ion having a m/z of about 281.3±0.5 to produce daughter ions having m/z of about 44.7±0.5, 61.8±0.5, 79.8±0.5, 143.1±0.5, 183.0±0.5, 194.9±0.5, 206.9±0.5, 209.0±0.5, 210.1±0.5, 223.1±0.5, 237.1±0.5, and 251.1±0.5. These parent and daughter ion peaks generated from tandem mass spectrometric fragmentation of oleic acid are illustrated in FIG. 5. For this example, the parent to parent transition of 281.3±0.5 to 281.3±0.5 was used for quantitation of oleic acid. The calibration range for oleic acid was determined to be 10.0 to 400 µg/mL.

Figure 6:
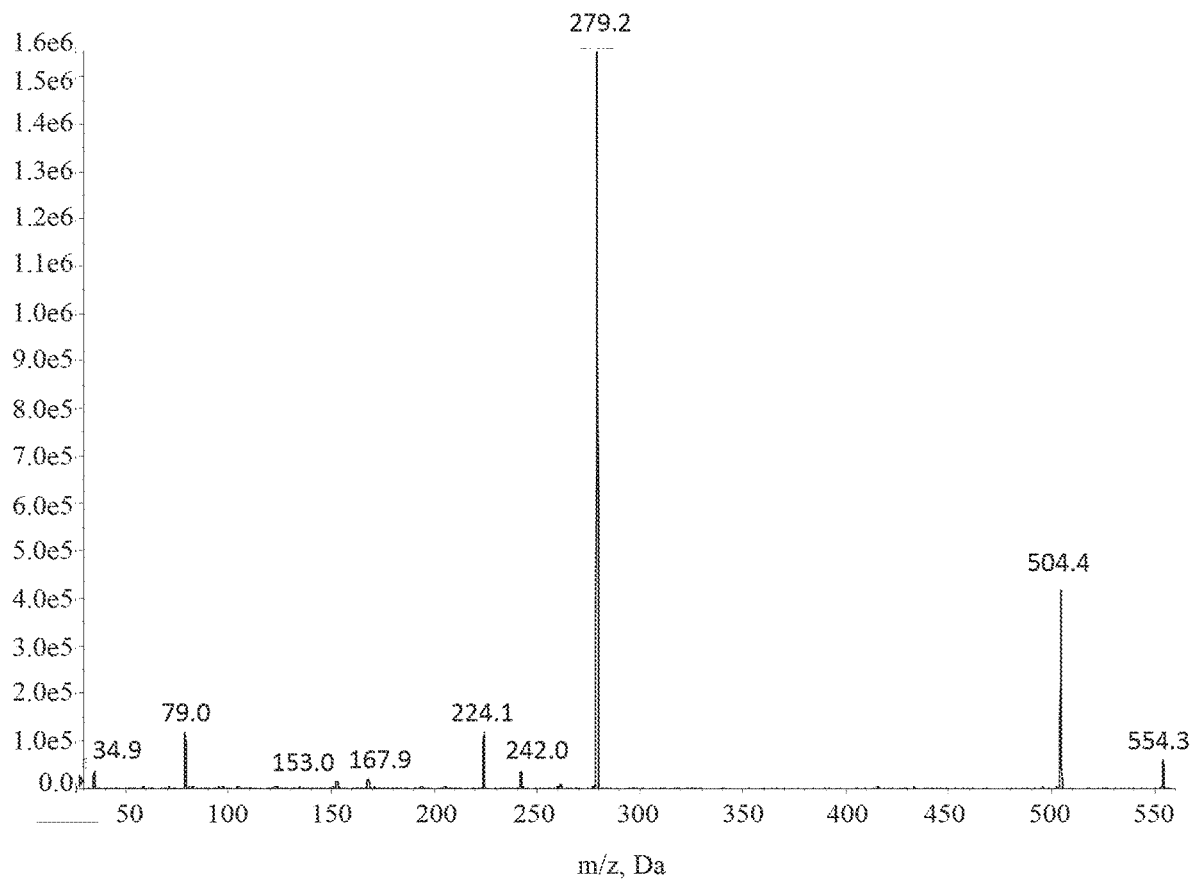
FIG. 6 shows exemplary parent and daughter ion peaks generated from tandem mass spectrometric fragmentation of LGPC.

MRM transitions that were monitored for the quantitation of LGPC in negative ionization mode include those produced by fragmenting a parent ion having a m/z of about 554.3±0.5 to produce daughter ions having m/z of about 279.2±0.5, 34.9±0.5, 79.0±0.5, 153.0±0.5, 167.9±0.5, 224.1±0.5, 242.0±0.5, and 504.4±0.5. These parent and daughter ion peaks generated from tandem mass spectrometric fragmentation of LGPC are illustrated in FIG. 6. Due to the zwitterionic nature of LGPC, a counter ion was used to quantify the analyte in negative ionization mode. In this example chloride was selected for use as the counter ion by including a small amount of ammonium chloride in the mobile phase and the transition of parent ion [M+Cl]⁻ to daughter ion m/z 279±0.5 was selected for quantitation of LGPC. The calibration range for LGPC was determined to be 2.50 to 100 µg/mL.

Figure 7:
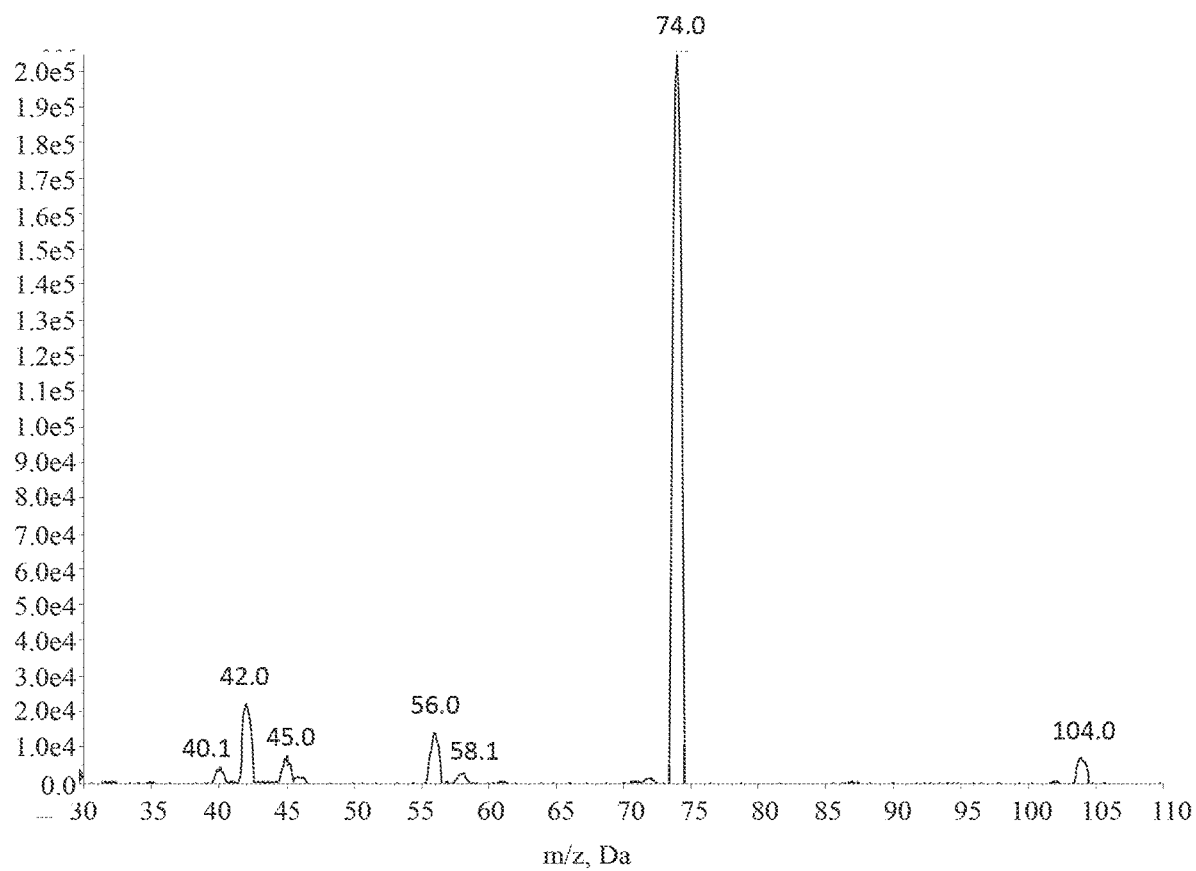
FIG. 7 shows exemplary parent and daughter ion peaks generated from tandem mass spectrometric fragmentation of serine.

MRM transitions that were monitored for the quantitation of serine in negative ionization mode include those produced by fragmenting a parent ion having a m/z of about 104.0±0.5 to produce daughter ions having m/z of about 74.0±0.5, 40.1±0.5, 42.0±0.5, 45.0±0.5, 56.0±0.5, and 58.1±0.5. These parent and daughter ion peaks generated from tandem mass spectrometric fragmentation of serine are illustrated in FIG. 7. In this example, the daughter ion used for quantitation of serine has a m/z of about 74.0±0.5. The calibration range for serine was determined to be 2.50 to 100 µg/mL.

As can be seen in the product ion scans in FIGS. 1-7, a plurality of daughter ions may be generated upon fragmentation of the indicated parent ions. Any one or more of these daughter ions indicated in FIGS. 1-7 or listed in Table 2 in the column headed "Additional Daughter Ions" may be selected to replace or augment the daughter ions used in the examples described above and in Table 2 in the column headed "Daughter Ion for Quantitation (m/z)".

As an alternative method to measure serine, chromatography under ion-pairing conditions was used (PFPA), and the mass spectrometer was operated in positive mode. Under these conditions, serine was chromatographically retained and not subject to a high level matrix suppression. For the serine PFPA method, the column heater was set at 60° C. Mobile phase A was 0.05% perfluoropentanoic acid (PFPA) in water, and mobile phase B was 0.05% PFPA in acetonitrile. Linear gradient elution was carried out with an initial condition of 1% mobile phase B held for 0.5 min and then increased to 39% in 1.1 min. The proportion of mobile phase B was increased to 80% (20% mobile phase A) in 0.2 min and then back to 1% (99% mobile phase A) in 0.1 min for equilibration for the next injection. The flow rate was 800 µL/min and the total run time was 2.21 min. An aliquot of 1.5 µL of the final extraction solution was injected for each sample.

For mass spectrometry with the serine PFPA method, the instruments were operated in positive MRM mode with ion pairs 106.1/60.1 and 109.1/63.1 for serine and serine-$d_3$, respectively. Ionspray voltage was set at 3.0 kV, source temperature at 550° C., and curtain gas at 20; nebulizer and desolvation gas flow rates were set at 70, and CAD gas at high. Declustering potential was set at 41 V, collision energy at 45 eV, entrance potential at 10 V, and collision cell exit potential at 8 V.

In another example, alternative methods were developed to measure individual analytes. In the methods exemplified below, liquid chromatography with a reversed phase column (Waters ACQUITY UPLC® BEH C18, 1.7 µm, 2.1×100 mm) was performed on extracted samples using Agilent 1290 Infinity UHPLC systems, each equipped with a binary solvent pump unit, a refrigerated autosampler (set at 4° C.), and a column heater (set at 60° C.). A single fixed aliquot of 0.5-1.0 µL of the final extraction solution was injected onto the chromatography column for each sample in each batch. The eluent from the chromatography column was directly and automatically introduced into the electrospray source of a mass spectrometer. Methanol was used for needle wash. AB Sciex QTrap 5500 mass spectrometers with Turbo V source (ESI) were used.

For these methods, the exemplary ions that were monitored for the quantitation of 2-HB, 3-HB, 4-MOP, oleic acid, LGPC, serine, and pantothenate are listed in Table 4.

TABLE 4

Ions useful for quantitation of analytes

| Analyte or Internal Std | Ionization Mode (Polarity) | Parent Ion | Daughter Ion |
|---|---|---|---|
| 2-Hydroxybutyric acid | Negative | 103.1 ± 0.5 | 57.1 ± 0.5 |
| 2-Hydroxybutyric acid-$d_3$ | Negative | 106.1 ± 0.5 | 59.1 ± 0.5 |
| 3-Hydroxybutyric acid | Negative | 103.1 ± 0.5 | 59.1 ± 0.5 |
| 3-Hydroxybutyric acid-$d_4$ | Negative | 107.1 ± 0.5 | 59.1 ± 0.5 |
| 4-Methyl-2-oxopentanoic acid | Negative | 128.8 ± 0.5 | 85.1 ± 0.5 |
| 4-Methyl-2-oxopentanoic acid-$d_3$ | Negative | 132.1 ± 0.5 | 88.1 ± 0.5 |
| Oleic Acid | Negative | 281.3 ± 0.5 | 281.3 ± 0.5 |
| Oleic Acid-$^{13}C_{18}$ | Negative | 299.3 ± 0.5 | 299.3 ± 0.5 |
| LGPC | Positive | 520.5 ± 0.5 | 184.2 ± 0.5 |
| LGPC-$d_9$ | Positive | 529.5 ± 0.5 | 193.2 ± 0.5 |
| Serine | Positive | 106.1 ± 0.5 | 60.1 ± 0.5 |
| Serine-$d_3$ | Positive | 109.1 ± 0.5 | 63.1 ± 0.5 |
| Pantothenate | Positive | 220.1 ± 0.5 | 124 ± 0.5 |
| Pantothenate-$^{13}C_3$—$^{15}N$ | Positive | 224.1 ± 0.5 | 126.1 ± 0.5 |

For example, methods were developed that measured the amount of 2-HB, 3-HB, 4-MOP, LGPC, or oleic acid. For these methods, mobile phase A was 0.0100% formic acid in water, and mobile phase B was acetonitrile/Methanol (1:1). Linear gradient elution was carried out with an initial condition of 5% mobile phase B. Mobile phase B was increased to 25% at 0.8 min, to 37% at 1.40 min, to 99% at 1.50 and 2.60 min, and then to 0.5% at 2.70 min. The flow rate was 550 µL/min. The mass spectrometer was operated in negative MRM mode for 2-HB, 3-HB, 4-MOP, or oleic acid and in positive MRM mode for LGPC.

In another example, methods were developed that measured the amount of pantothenate or serine. For these methods, mobile phase A was 0.0500% perfluoropenanoic acid (PFPA) in water, and mobile phase B was 0.0500% PFPA in acetonitrile. Linear gradient elution was carried out with an initial condition of 1% mobile phase B. Mobile phase B was maintained at 1% at 0.5 min, increased to 16% at 2.50 min, to 46% at 3.50 min, and was decreased to 1.0% at 3.60 min and at 4.50 min. The flow rate was 800 µL/min. The mass spectrometer was operated in positive MRM mode.

Example 2: LC-MS/MS Measurement of a Plurality of Analytes

Methods were developed to measure a plurality of analytes in a sample using a single injection of a sample extract; that is, the amount of two or more analytes was determined in the same sample using the same (single) injection. In all methods exemplified below, liquid chromatography with a reversed phase column (Waters ACQUITY UPLC® BEH C18, 1.7 µm, 2.1×100 mm) was performed on extracted samples using Agilent 1290 Infinity UHPLC systems, each equipped with a binary solvent pump unit, a refrigerated autosampler (set at 4° C.), and a column heater (set at 50° C. unless otherwise indicated).

LC-MS/MS Method 1: Serine and Pantothenate

For example, a method was developed that measured the amount of pantothenate and serine in the same injection. In this method, the column heater was set at 60° C., mobile phase A was 0.0500% perfluoropenanoic acid (PFPA) in water, and mobile phase B was 0.0500% PFPA in acetonitrile. Linear gradient elution was carried out with an initial condition of 1% mobile phase B. Mobile phase B was maintained at 1% at 0.5 min, increased to 16% at 2.50 min, to 46% at 3.50 min, and was decreased to 1.0% at 3.60 min and at 4.50 min. The flow rate was 800 µL/min. For each sample analyzed, a single fixed aliquot of 0.5-1.0 µL of the final extraction solution was injected onto the chromatography column. The eluent from the chromatography column was directly and automatically introduced into the electrospray source of a mass spectrometer. Methanol was used for needle wash. AB Sciex QTrap 5500 mass spectrometers with Turbo V source (ESI) operated in positive MRM mode were used. Exemplary ions that may be monitored for the quantitation of serine, and pantothenate in positive MRM mode are listed in Table 4. Quantitation was performed using a weighted linear least squares regression analysis generated from fortified calibration standards prepared immediately prior to each run. In this example, plasma samples from 64 individuals were analyzed, and the analyte levels obtained using the described method are shown in Table 5.

LC-MS/MS Method 2: (2-HB, 3-HB, 4-MOP, LGPC, and Oleic Acid)

In another example, a method was developed that measured the amount of one or more, two or more, and up to all five analytes selected from 2-HB, 3-HB, 4-MOP, LGPC, and oleic acid, in a single injection with the mass spectrometer operated in positive MRM mode and negative MRM mode. For this method, the column heater was set at 60° C., mobile phase A was 0.0100% formic acid in water, and mobile phase B was acetonitrile/Methanol (1:1). Linear gradient elution was carried out with an initial condition of 5% mobile phase B. Mobile phase B was increased to 25% at 0.8 min, to 37% at 1.40 min, to 99% at 1.50 and 2.60 min, and then to 0.5% at 2.70 min. The flow rate was 550 µL/min. A single fixed aliquot of 0.5-1.0 µL of the final extraction solution was injected onto the chromatography column for each sample. The eluent from the chromatography column was directly and automatically introduced into the electrospray source of a mass spectrometer. Methanol was used for needle wash. AB Sciex QTrap 5500 mass spectrometers with Turbo V source (ESI) operated in negative MRM mode for 2-HB, 3-HB, 4-MOP, and oleic acid and in positive MRM mode for LGPC were used. Exemplary ions that may be monitored for the quantitation of 2-HB, 3-HB, 4-MOP, oleic acid, and LGPC are listed in Table 4.

LC-MS/MS Method 3: (2-HB, 3-HB, 4-MOP, LGPC, and Oleic Acid)

Another method was developed to measure the amount of one or more, two or more, and up to all five analytes selected from 2-HB, 3-HB, 4-MOP, LGPC, and oleic acid in a single injection with the mass spectrometer operated in negative MRM mode only. Plasma samples from 64 individuals were spiked with isotopically labeled internal standards and subjected to protein precipitation with methanol. Following centrifugation, an aliquot of the supernatant was injected onto an Agilent 1290/AB Sciex QTrap 5500 LC/MS/MS system equipped with a $C_{18}$ reversed phase column and operated in negative MRM mode. The peak areas of the respective product ions were measured against the peak areas of the respective internal standard product ions. Exemplary ions that may be monitored for the quantitation of 2-HB, 3-HB, 4-MOP, oleic acid, and LGPC in negative MRM mode are listed in Table 2. Quantitation was performed using a weighted linear least squares regression analysis generated from fortified calibration standards prepared immediately prior to each run. The analyte levels obtained using the described method are shown in Table 5.

Table 5

Analyte concentrations measured in Plasma using Method 1 (Serine, Pantothenate) and Method 3 (2-HB, 3-HB, 4-MOP, LGPC, and Oleic Acid)

| Sample Number | Analyte Concentration (µg/ml) | | | | | | |
|---|---|---|---|---|---|---|---|
| | 2-HB | 3-HB | 4-MOP | LGPC | oleic acid | pantothenate | serine |
| 1 | 2.37 | 4.06 | 4.15 | 9.52 | 58.6 | 0.0341 | 7.27 |
| 2 | 3.53 | 1.48 | 2.7 | 18.4 | 43.3 | 0.118 | 8.82 |
| 3 | 2.28 | 1.43 | 2.75 | 18.2 | 30.5 | 0.15 | 12.6 |
| 4 | 3.95 | 4.61 | 2.97 | 12.4 | 56.9 | 0.0772 | 11.3 |
| 5 | 1.61 | 0.855 | 2.66 | 16.5 | 18.3 | 0.0337 | 10 |
| 6 | 6.22 | 3 | 5.34 | 13.8 | 41.3 | 0.0526 | 8.87 |
| 7 | 4.86 | 0.609 | 1.7 | 13.3 | 15.8 | 0.0342 | 5.63 |
| 8 | 3.67 | 1.46 | 2.83 | 16.1 | 42.1 | 0.0335 | 5.75 |
| 9 | 4.92 | 3.44 | 5.55 | 23.1 | 23.8 | 0.011 | 14.6 |
| 10 | 4.38 | 3.96 | 4.92 | 28.6 | 46 | 0.0523 | 10.5 |
| 11 | 5.34 | 5.48 | 3.09 | 10.2 | 75.9 | 0.0478 | 10.9 |
| 12 | 12 | 34 | 4.48 | 6.6 | 65 | 0.0495 | 7.62 |
| 13 | 5.31 | 2.36 | 4.83 | 19.8 | 45.8 | 0.121 | 8.13 |
| 14 | 5.43 | 13.3 | 2.78 | 22.8 | 68.4 | 0.0317 | 8.34 |
| 15 | 18.9 | 35.7 | 6.13 | 15.3 | 99.3 | 0.14 | 8.16 |
| 16 | 4.58 | 8.07 | 3.27 | 16 | 50.8 | 0.245 | 13.6 |
| 17 | 1.96 | 0.958 | 4.73 | 21.4 | 12.7 | 0.0279 | 11.8 |
| 18 | 8.38 | 1.94 | 4.68 | 16 | 38.2 | 0.138 | 11.6 |
| 19 | 3.89 | 4.01 | 4.67 | 8.62 | 58.5 | 0.0274 | 9.43 |
| 20 | 0.948 | 4.07 | 1.12 | 13.1 | 39.1 | 0.0327 | 14.7 |
| 21 | 10.2 | 27.6 | 4.21 | 9.18 | 135 | 0.051 | 11.8 |
| 22 | 7.17 | 3.99 | 3.26 | 23.6 | 28.2 | 0.127 | 9.59 |
| 23 | 5.79 | 3.24 | 3.1 | 17.1 | 75.6 | 0.0435 | 8.67 |
| 24 | 3.66 | 2.21 | 4.49 | 20.2 | 29.3 | 0.134 | 10.8 |
| 25 | 4.96 | 5.51 | 2.71 | 13 | 70.9 | 0.0274 | 14.4 |
| 26 | 4.81 | 5.69 | 4.59 | 8.53 | 46 | 0.0829 | 6.3 |
| 27 | 2.07 | 1.63 | 2.4 | 26 | 11.6 | 0.301 | 9.97 |
| 28 | 4.6 | 0.868 | 2.69 | 19.5 | 10.9 | 0.0344 | 14.4 |
| 29 | 9.66 | 1.28 | 2.15 | 12 | 10.2 | 0.0459 | 9.66 |
| 30 | 2.2 | 2.39 | 3.73 | 27.8 | 14 | 0.022 | 7.38 |

Table 5-continued

Analyte concentrations measured in Plasma using Method 1 (Serine, Pantothenate) and Method 3 (2-HB, 3-HB, 4-MOP, LGPC, and Oleic Acid)

| Sample Number | Analyte Concentration (μg/ml) | | | | | | |
|---|---|---|---|---|---|---|---|
| | 2-HB | 3-HB | 4-MOP | LGPC | oleic acid | pantothenate | serine |
| 31 | 3.66 | 2.22 | 5.24 | 14.7 | 39 | 0.0565 | 9.85 |
| 32 | 10.5 | 22.2 | 6.9 | 28.1 | 69.3 | 0.11 | 11.1 |
| 33 | 1.46 | 1.49 | 0.975 | 24.4 | 13.9 | 0.018 | 9.43 |
| 34 | 4.71 | 11.8 | 3.17 | 14.9 | 54.6 | 0.139 | 9.08 |
| 35 | 4.59 | 11.5 | 2.59 | 13.8 | 59 | 0.0976 | 11.4 |
| 36 | 4.38 | 3.35 | 3.21 | 16.2 | 28.2 | 0.0228 | 8.42 |
| 37 | 3.59 | 7.62 | 3.25 | 22.5 | 106 | 0.0679 | 7.79 |
| 38 | 3.81 | 1.65 | 1.68 | 12.2 | 43.6 | 0.0359 | 9.55 |
| 39 | 4.17 | 1.98 | 4.27 | 18 | 20 | 0.227 | 12.7 |
| 40 | 4.51 | 2.32 | 3.69 | 25.7 | 45.5 | 0.124 | 12.2 |
| 41 | 4.12 | 1.69 | 3.1 | 9.22 | 32.2 | 0.138 | 6.92 |
| 42 | 12.1 | 35.5 | 4.64 | 11 | 85.6 | 0.265 | 11.7 |
| 43 | 2.75 | 2.89 | 3.4 | 23.4 | 38.6 | 0.0336 | 9.34 |
| 44 | 4.91 | 2.38 | 4.93 | 16.1 | 103 | 0.0522 | 5.95 |
| 45 | 9.2 | 8.54 | 6.11 | 11.5 | 56.3 | 0.0843 | 5.32 |
| 46 | 4.52 | 4.11 | 3.91 | 9.13 | 58.1 | 0.0435 | 9.91 |
| 47 | 3.11 | 21.7 | 3.73 | 24.5 | 69.3 | 0.179 | 11.8 |
| 48 | 2.48 | 1.79 | 3.41 | 21.6 | 46.5 | 0.0203 | 10.3 |
| 49 | 2.28 | 1.26 | 4.51 | 11 | 34.8 | 0.031 | 8.34 |
| 50 | 6.18 | 3.51 | 4.31 | 8.5 | 67.3 | 0.0363 | 10.1 |
| 51 | 3.14 | 2.96 | 2.53 | 12.6 | 66.3 | 0.174 | 9.87 |
| 52 | 1.44 | 0.842 | 2.68 | 34.8 | 9.57 | 0.0168 | 9.3 |
| 53 | 3.28 | 3.22 | 3.38 | 13.6 | 38.6 | 0.0313 | 10.7 |
| 54 | 1.65 | 2.07 | 1.53 | 23.1 | 55.2 | 0.0195 | 9.83 |
| 55 | 4.95 | 3.67 | 3.49 | 8.47 | 43.3 | 0.332 | 10.3 |
| 56 | 5.44 | 7.06 | 2.84 | 15.5 | 49.1 | 0.306 | 10.1 |
| 57 | 5.54 | 2.37 | 2.39 | 22.6 | 28.8 | 0.156 | 7.09 |
| 58 | 3.47 | 1.18 | 2.51 | 20.3 | 13.6 | 0.0857 | 12.7 |
| 59 | 10 | 13.1 | 3.39 | 16.6 | 127 | 0.057 | 7.35 |
| 60 | 1.63 | 1.22 | 1 | 13.5 | 11.9 | 0.0272 | 8.81 |
| 61 | 4.03 | 4.03 | 3.13 | 13.2 | 53.1 | 0.0511 | 7.82 |
| 62 | 3.39 | 4.09 | 2.63 | 14.1 | 53 | 0.164 | 8.61 |
| 63 | 4.76 | 3.84 | 3.12 | 15.7 | 29.3 | 0.211 | 6.88 |
| 64 | 4.09 | 3.21 | 4.05 | 28.8 | 61.3 | 0.0281 | 9.29 |

LC-MS/MS Method 4: (2-HB, 3-HB, 4-MOP, LGPC, Oleic Acid, Serine, and Pantothenate)

Figure 8A:
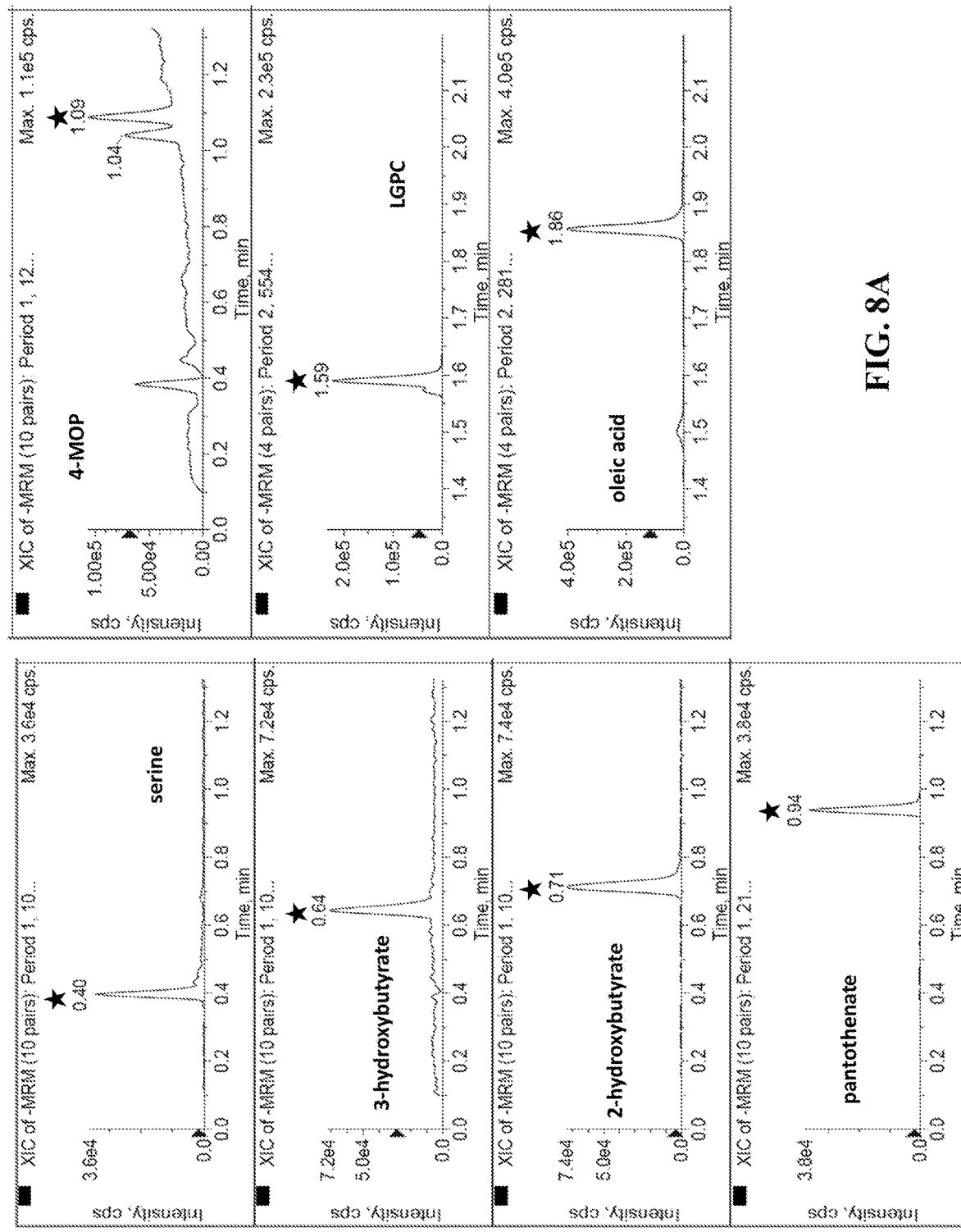
FIG. 8A shows chromatograms of serine, 3-HB, 2-HB, pantothenate, 4-MOP, LGPC, and oleic acid. For each analyte, the peak of interest, with associated retention time, is indicated by a star. The data was generated using Method 4 as described in Example 2.
Figure 8B:
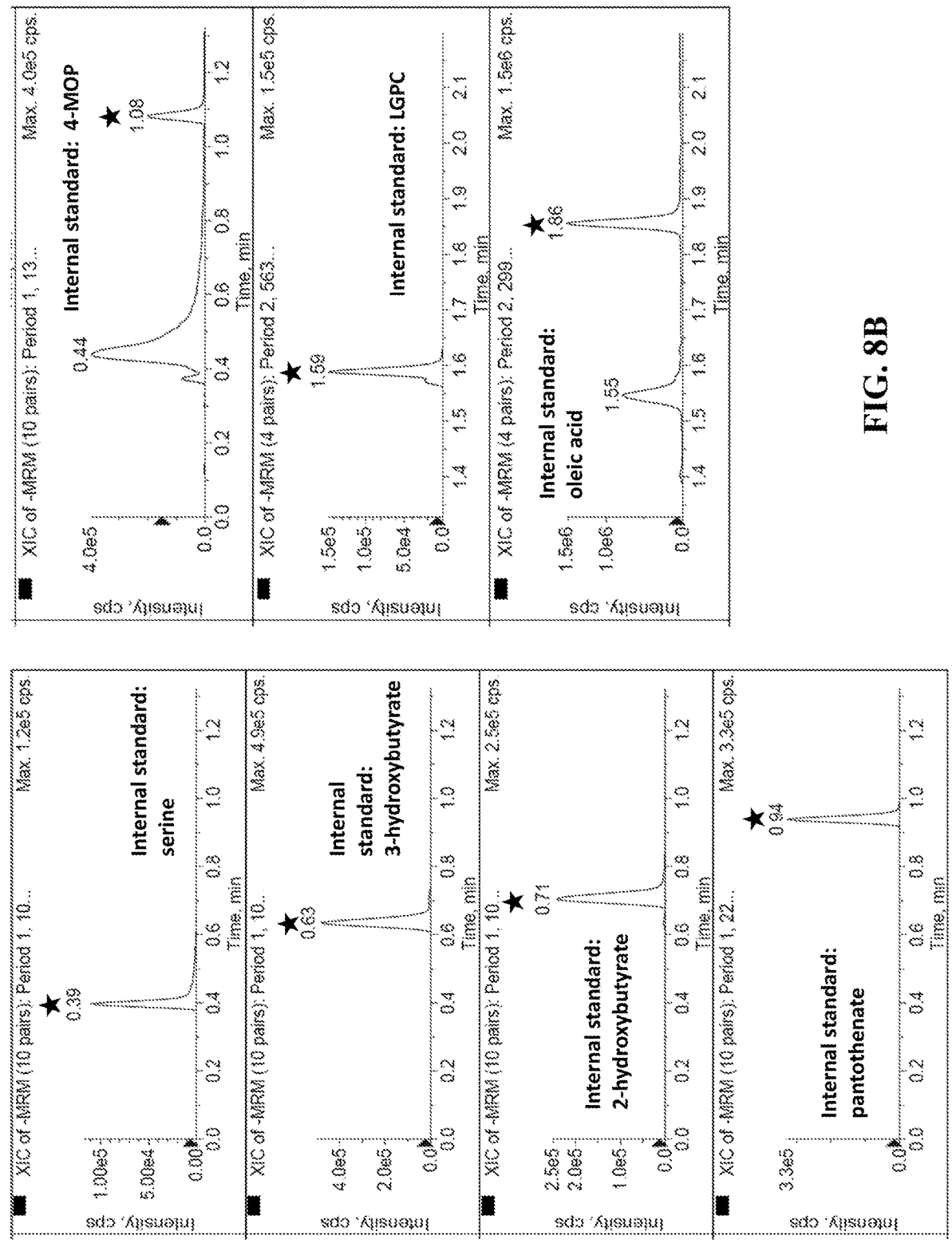
FIG. 8B shows chromatograms of the internal standards of serine-$d_3$, 3-HB-$d_4$, 2-HB-$d_3$, pantothenate-$^{13}C_3$-$^{15}N$, 4-MOP-$d_3$, LGPC-$d_9$, and oleic acid-$^{13}C_{18}$. For each internal standard, the peak of interest, with associated retention time, is indicated by a star. The data was generated using Method 4 as described in Example 2.

In another example, a method was developed that measured the amount of one or more, two or more, and up to all seven analytes selected from 2-HB, 3-HB, 4-MOP, LGPC, oleic acid, serine, and pantothenate, in a single injection with the mass spectrometer operated in negative MRM mode. Plasma samples from 73 individuals and serum samples from 30 individuals were prepared and subjected to reversed phase liquid chromatography as described above in the General Methods. The described reversed phase chromatography method separated a plurality of up to seven analytes with good peak shapes. Peaks for all seven analytes are shown in FIG. 8A, and peaks from corresponding internal standards are shown in FIG. 8B. The described method obtained separation of the metabolites 4-MOP and 3-MOP, as shown in FIG. 8A, with a retention time of 1.09 min for 4-MOP and 1.04 min for 3-MOP. Retention time for the peak of interest for each analyte (and corresponding internal standard) is indicated by a star.

MS/MS was performed on the separated samples using AB Sciex QTrap 5500 mass spectrometers. The instruments were operated in negative multiple reaction monitoring (MRM) mode, and the method was divided into two periods with the second period starting at 1.33 min. The first period detected 2-HB, 3-HB, 4-MOP, serine, and pantothenate, and the second period detected oleic acid and LGPC. For both periods, ionspray voltage was set at −4.5 kV, source temperature at 550° C., curtain gas at 30, and nebulizer and desolvation gas flow rates at 70, collisionally activated dissociation (CAD) gas at low. Detailed MS settings are described in Table 1. All analytes were found to ionize well in negative mode under electrospray conditions which was unexpected since serine, LGPC and pantothenate are normally measured using positive mode conditions. The ions monitored for quantitation in this method are the daughter ions listed in Table 2, except for oleic acid where the parent ion was monitored. Additional exemplary ions that may be monitored for the quantitation of 2-HB, 3-HB, 4-MOP, oleic acid, LGPC, pantothenate, and serine in negative MRM mode are listed in Table 2 ("Additional daughter ions" column).

Raw data were acquired and processed using Analyst 1.6.2 software (SciEx). For quantitation, peak area ratios of analyte to internal standard were fitted against the concentrations of the calibration standards by weighted ($1/x^2$) linear least squares regression. The resulting slope and intercept of the calibration curve were used to calculate the concentrations in experimental samples. Parent and daughter ions for quantitation of analytes and corresponding internal standards are shown in Table 2. The LC-MS/MS method described in this example resulted in the quantitation of a plurality of up to seven analytes in a single injection with a run time of 2.21 minutes. The analyte levels obtained for the 30 serum samples using LC-MS/MS Method 4 are shown in Table 6. Analyte levels were similar for plasma and serum samples.

TABLE 6

Analyte concentrations measured (Serum samples)

Analyte Concentration (μg/ml)

| Sample Number | 2-HB | 3-HB | 4-MOP | LGPC | oleic acid | pantothenate | serine |
|---|---|---|---|---|---|---|---|
| 1 | 6.45 | 11.9 | 4.56 | 6.61 | 61.1 | 0.0306 | 13.2 |
| 2 | 4.73 | 5.78 | 5.42 | 21.9 | 39.1 | 0.0632 | 12 |
| 3 | 2.64 | 0.776 | 3.42 | 14 | 6.63 | 0.0235 | 16.2 |
| 4 | 9.05 | 19.4 | 6.21 | 15.4 | 87.4 | 0.06 | 13.1 |
| 5 | 3.13 | 1.35 | 4.41 | 16 | 26.8 | 0.0484 | 14.4 |
| 6 | 3.15 | 1.97 | 3.89 | 19.8 | 27.8 | 0.0353 | 11.3 |
| 7 | 5.28 | 1.98 | 7.21 | 19.7 | 42.4 | 0.0272 | 11.9 |
| 8 | 4.52 | 2.56 | 6.45 | 19 | 32.9 | 0.0437 | 8.2 |
| 9 | 2.44 | 2.09 | 3.54 | 34.7 | 27.4 | 0.0338 | 13.4 |
| 10 | 5.61 | 24.4 | 4.04 | 10.2 | 86.2 | 0.144 | 7.2 |
| 11 | 7.36 | 25.3 | 4.2 | 21.9 | 94.3 | 0.0355 | 8.51 |
| 12 | 7.35 | 8.74 | 5.71 | 16.8 | 27.3 | 0.0583 | 7.6 |
| 13 | 3.32 | 1.25 | 5.45 | 27.9 | 20.6 | 0.0323 | 9.18 |
| 14 | 6.39 | 23.6 | 5.89 | 18.6 | 71.1 | 0.0524 | 12.6 |
| 15 | 4.09 | 0.929 | 5.23 | 14.8 | 21.3 | 0.0287 | 8.39 |
| 16 | 4.9 | 8.43 | 5.5 | 21 | 53.1 | 0.0273 | 9.95 |
| 17 | 5.87 | 17.6 | 3.7 | 17.3 | 77.8 | 0.0266 | 13.3 |
| 18 | 3.72 | 1.66 | 4.91 | 18.7 | 15.3 | 0.0145 | 11.8 |
| 19 | 5.92 | 9.91 | 4.45 | 9.36 | 55 | 0.0837 | 18.1 |
| 20 | 2.05 | 10.2 | 2.38 | 9.63 | 55.4 | 0.025 | 11.1 |
| 21 | 5.35 | 9.04 | 4.31 | 15.3 | 91.5 | 0.0256 | 11.1 |
| 22 | 1.83 | 1.12 | 3.06 | 21.7 | 4.65 | 0.0515 | 8.37 |
| 23 | 3.81 | 8.51 | 2.97 | 14.7 | 57.5 | 0.0461 | 11.7 |
| 24 | 1.02 | 1.54 | 2.58 | 22.8 | 39.4 | 0.0301 | 11.2 |
| 25 | 4.81 | 2.79 | 3.16 | 9.13 | 54 | 0.0554 | 10.6 |
| 26 | 6.34 | 56.7 | 4.37 | 8.68 | 81.3 | 0.047 | 17.1 |
| 27 | 3.76 | 1.75 | 4.04 | 11.4 | 39 | 0.0264 | 9.24 |
| 28 | 5.67 | 14.1 | 3.48 | 19.1 | 106 | 0.0221 | 11.8 |
| 29 | 3.23 | 1.93 | 2.52 | 26.4 | 41.5 | 0.0223 | 11.3 |
| 30 | 10.1 | 6.97 | 4.52 | 11.8 | 53.7 | 0.0464 | 9.19 |

Analytical Validation of LC-MS/MS Method 4

The analytical performance of LC-MS/MS Method 4 was validated on three identical LC-MS/MS systems using plasma samples.

The precision of the method for measuring a plurality of the seven analytes in a single injection was evaluated at three QC levels (low, mid, and high) in plasma samples. The evaluation was performed using three identical instrument systems and the precision obtained for each QC level was determined for each instrument individually and for the three instruments as a whole. Five replicates per QC level were analyzed in each run, with five runs analyzed per instrument. A total of 25 replicates per QC level were included in the inter-run CV calculations for each individual instrument and all 75 replicates included per QC level for the overall inter-run CV calculations. For overall CV calculations (all three instruments), the inter-run CVs were less than 5.8% at each QC level. The results are presented in Table 7. The intra-run CVs for all analytes on each instrument were less than 5.5% for each QC level. Linear responses ($R^2 > 0.99$) were observed over a 40 fold range for 4-MOP, LGPC, oleic acid, and serine, and over an 80 fold range for 2-HB, 3-HB, and pantothenate. Calibration ranges were selected based on analysis of over 2500 individual samples.

TABLE 7

Inter-run Precision for a Plurality of Analytes on Three LC/MS Systems.

| QC Level/ Parameter | LC/MS | 2-HB | LGPC | Oleic Acid | 4-MOP | 3-HB | Serine | Pantothenate |
|---|---|---|---|---|---|---|---|---|
| Low Mean (μg/mL) | 1 (n = 5 × 5) | 2.44 | 17.5 | 35.5 | 2.11 | 2.59 | 7.81 | 0.0299 |
| | 2 (n = 5 × 5) | 2.53 | 17.1 | 35.4 | 2.10 | 2.62 | 7.71 | 0.0311 |
| | 3 (n = 5 × 5) | 2.50 | 18.6 | 36.2 | 2.07 | 2.57 | 7.89 | 0.0309 |
| | All (n = 75) | 2.49 | 17.7 | 35.7 | 2.09 | 2.59 | 7.80 | 0.0306 |
| Low % CV | 1 (n = 5 × 5) | 2.3 | 4.6 | 2.8 | 3.9 | 3.3 | 4.4 | 3.1 |
| | 2 (n = 5 × 5) | 2.1 | 2.0 | 2.5 | 3.0 | 3.8 | 4.5 | 2.8 |
| | 3 (n = 5 × 5) | 2.4 | 2.5 | 3.5 | 4.3 | 3.4 | 3.2 | 3.6 |
| | All (n = 75) | 2.7 | 4.9 | 3.1 | 3.8 | 3.6 | 4.1 | 3.6 |
| Mid Mean (μg/mL) | 1 (n = 5 × 5) | 3.99 | 9.94 | 56.0 | 4.60 | 5.23 | 10.5 | 0.0437 |
| | 2 (n = 5 × 5) | 4.12 | 9.67 | 56.8 | 4.60 | 5.42 | 10.3 | 0.0453 |
| | 3 (n = 5 × 5) | 4.03 | 10.5 | 56.5 | 4.60 | 5.25 | 10.5 | 0.0447 |
| | All (n = 75) | 4.05 | 10.1 | 56.4 | 4.60 | 5.3 | 10.4 | 0.0446 |
| Mid % CV | 1 (n = 5 × 5) | 2.7 | 5.8 | 2.5 | 3.4 | 1.9 | 4.5 | 2.9 |
| | 2 (n = 5 × 5) | 1.8 | 1.4 | 2.7 | 2.2 | 1.7 | 4.8 | 2.1 |
| | 3 (n = 5 × 5) | 2.2 | 2.9 | 3.4 | 2.8 | 2.4 | 3.3 | 2.9 |
| | All (n = 75) | 2.6 | 5.3 | 2.9 | 2.8 | 2.5 | 4.3 | 3.0 |

TABLE 7-continued

Inter-run Precision for a Plurality of Analytes on Three LC/MS Systems.

| QC Level/ Parameter | LC/MS | 2-HB | LGPC | Oleic Acid | 4-MOP | 3-HB | Serine | Pantothenate |
|---|---|---|---|---|---|---|---|---|
| High Mean (μg/mL) | 1 (n = 5 × 5) | 7.74 | 26.6 | 120 | 8.59 | 19.7 | 14.8 | 0.0874 |
| | 2 (n = 5 × 5) | 7.97 | 26.1 | 120 | 8.46 | 20.4 | 14.2 | 0.0899 |
| | 3 (n = 5 × 5) | 7.78 | 27.9 | 120 | 8.43 | 19.9 | 14.7 | 0.0889 |
| | All (n = 75) | 7.83 | 26.9 | 120 | 8.49 | 20.0 | 14.6 | 0.0887 |
| High % CV | 1 (n = 5 × 5) | 1.8 | 4.1 | 2.4 | 2.4 | 1.7 | 3.8 | 2.8 |
| | 2 (n = 5 × 5) | 2.0 | 2.1 | 3.2 | 3.1 | 1.1 | 3.5 | 2.0 |
| | 3 (n = 5 × 5) | 2.3 | 2.6 | 2.9 | 2.2 | 2.1 | 3.2 | 2.4 |
| | All (n = 75) | 2.4 | 4.2 | 2.8 | 2.7 | 2.4 | 3.8 | 2.6 |

Accuracy and precision at the LLOQ were evaluated on all three LC/MS instrument systems. The signal-to-noise ratio for every analyte was greater than 5:1. Five replicates of the LLOQ samples (prepared in fatty-acid free BSA solution) were analyzed in each run, with five runs analyzed per instrument. A total of 25 replicates of the LLOQ were included in the inter-run calculations per instrument, with 75 replicates included in the combined instrument data. All intra- and inter-run inaccuracies were less than 16% and CVs were less than 9.9%; the data are shown in Table 8. These results indicated that quantitation of the plurality of analytes at the lower limit was highly accurate and precise.

TABLE 8

Inter- and Intra-Run Accuracy and Precision at the LLOQ.

| | | | LLOQ Concentration (μg/mL) | | | | | | |
|---|---|---|---|---|---|---|---|---|---|
| | | | 0.5 | 2.5 | 10 | 0.5 | 1 | 2.5 | 0.01 |
| LC/MS | Parameter | Run ID | 2-HB | LGPC | Oleic Acid | 4-MOP | 3-HB | Serine | Pantothenate |
| 1 | % Accuracy | Run 1 (n = 5) | 109 | 100 | 105 | 100 | 105 | 104 | 95.6 |
| | | Run 2 (n = 5) | 98.7 | 104 | 111 | 92.6 | 103 | 98.3 | 103 |
| | | Run 3 (n = 5) | 98.3 | 102 | 111 | 107 | 105 | 99.3 | 107 |
| | | Run 4 (n = 5) | 108 | 104 | 115 | 104 | 98.7 | 105 | 97.7 |
| | | Run 5 (n = 5) | 102 | 102 | 116 | 97.9 | 105 | 88.7 | 91.3 |
| | | Inter-Run (n = 25) | 103 | 102 | 112 | 100 | 103 | 99 | 99.1 |
| | % CV | Run 1 (n = 5) | 2.9 | 1.1 | 1.4 | 1.9 | 5.8 | 4.9 | 5 |
| | | Run 2 (n = 5) | 2.7 | 0.7 | 3.9 | 5.8 | 3 | 3.3 | 3.3 |
| | | Run 3 (n = 5) | 4.6 | 0.9 | 2.5 | 4.7 | 3.5 | 3.7 | 5.6 |
| | | Run 4 (n = 5) | 3.9 | 2.1 | 1.9 | 8.5 | 2.8 | 6.7 | 3.8 |
| | | Run 5 (n = 5) | 2.4 | 1.8 | 3.1 | 5.6 | 2.2 | 4.5 | 7.4 |
| | | Inter-Run (n = 25) | 3.3 | 1.3 | 2.6 | 5.3 | 3.5 | 4.6 | 5 |
| 2 | % Accuracy | Run 1 (n = 5) | 99.9 | 103 | 111 | 101 | 102 | 107 | 95.2 |
| | | Run 2 (n = 5) | 99.2 | 102 | 104 | 108 | 98.2 | 92.9 | 102 |
| | | Run 3 (n = 5) | 99.1 | 104 | 112 | 97.4 | 98.1 | 109 | 101 |
| | | Run 4 (n = 5) | 105 | 103 | 104 | 95.4 | 96.2 | 106 | 97.7 |
| | | Run 5 (n = 5) | 101 | 103 | 106 | 92.4 | 93.6 | 95.3 | 95.8 |
| | | Inter-Run (n = 25) | 101 | 103 | 107 | 98.8 | 97.5 | 102 | 98.3 |
| | % CV | Run 1 (n = 5) | 1.5 | 1.9 | 5.2 | 2.8 | 1.8 | 2.7 | 4.7 |
| | | Run 2 (n = 5) | 2.1 | 2.5 | 5.1 | 3.6 | 1.7 | 4.3 | 4.1 |
| | | Run 3 (n = 5) | 2.6 | 1.8 | 3.9 | 2.8 | 2.7 | 4.6 | 6 |
| | | Run 4 (n = 5) | 0.3 | 1.4 | 5.1 | 3.8 | 2 | 7.8 | 3.6 |
| | | Run 5 (n = 5) | 0.7 | 1.4 | 2.9 | 4.6 | 4.4 | 2.8 | 3 |
| | | Inter-Run (n = 25) | 1.4 | 1.8 | 4.5 | 3.5 | 2.5 | 4.4 | 4.3 |
| 3 | % Accuracy | Run 1 (n = 5) | 103 | 100 | 112 | 108 | 102 | 97.5 | 101 |
| | | Run 2 (n = 5) | 102 | 97 | 112 | 95.5 | 102 | 98.7 | 107 |
| | | Run 3 (n = 5) | 99 | 103 | 117 | 103 | 97.3 | 102 | 103 |
| | | Run 4 (n = 5) | 95.3 | 101 | 119 | 105 | 101 | 96.5 | 102 |
| | | Run 5 (n = 5) | 100 | 98 | 107 | 110 | 89.4 | 92 | 100 |
| | | Inter-Run (n = 25) | 100 | 100 | 113 | 104 | 98.3 | 97.3 | 102 |
| | % CV | Run 1 (n = 5) | 2.4 | 2.1 | 2.9 | 6.7 | 3.6 | 5.4 | 3.8 |
| | | Run 2 (n = 5) | 2.2 | 2 | 1.3 | 9.9 | 3.6 | 3.5 | 2.8 |
| | | Run 3 (n = 5) | 3.5 | 0.8 | 4 | 7.3 | 5.3 | 4.2 | 3 |
| | | Run 4 (n = 5) | 2.4 | 2.1 | 3.1 | 7.4 | 2.9 | 4.2 | 1.2 |
| | | Run 5 (n = 5) | 2.9 | 2.8 | 4 | 6.4 | 2.6 | 3.9 | 3 |
| | | Inter-Run (n = 25) | 2.7 | 2 | 3.1 | 7.6 | 3.6 | 4.2 | 2.8 |
| All | % Accuracy | All Runs (n = 75) | 101 | 102 | 111 | 101 | 100 | 99.4 | 100 |

TABLE 8-continued

Inter- and Intra-Run Accuracy and Precision at the LLOQ.

| | | | LLOQ Concentration (μg/mL) | | | | | | |
|---|---|---|---|---|---|---|---|---|---|
| LC/MS | Parameter | Run ID | 0.5 2-HB | 2.5 LGPC | 10 Oleic Acid | 0.5 4-MOP | 1 3-HB | 2.5 Serine | 0.01 Pantothenate |
| | % CV | All Runs (n = 75) | 2.5 | 1.7 | 3.4 | 5.5 | 3.2 | 4.4 | 4 |

In order to assess the recovery of analytes during the extraction, plasma QC samples were fortified with known concentrations of analytes. Six replicates of the spiked plasma QC samples were extracted and analyzed along with regular plasma QC samples. Recovery of the spiked amount was calculated after subtraction of the amount in the regular QC samples. The recoveries were determined to be 96.3 to 103% for the seven analytes. The data are presented in Table 9.

method. A method developed and validated for the quantitation of serine alone was used in combination with the reversed phase liquid chromatography MS/MS methods for the measurement of a plurality of analytes (multi-analyte method).

A total of 318 patient plasma samples in five batches were analyzed using the serine alone PFPA method (serine PFPA, LC-MS/MS Method 1) and the multi-analyte method. The results were compared using Bland-Altman plots as shown

TABLE 9

Recovery of Analytes

| | 2-HB | | LGPC | | Oleic Acid | | 4-MOP | | 3-HB | | Serine | | Pantothenate | |
|---|---|---|---|---|---|---|---|---|---|---|---|---|---|---|
| Replicate | Mid QC. (μg/mL) | Spiked Mid QC (μg/mL) | Mid QC. (μg/mL) | Spiked Mid QC (μg/mL) | Mid QC. (μg/mL) | Spiked Mid QC (μg/mL) | Mid QC. (μg/mL) | Spiked Mid QC (μg/mL) | Mid QC. (μg/mL) | Spiked Mid QC (μg/mL) | Mid QC. (μg/mL) | Spiked Mid QC (μg/mL) | Mid QC. (μg/mL) | Spiked Mid QC (μg/mL) |
| 1 | 3.98 | 8.82 | 9.73 | 36.1 | 55.6 | 153 | 4.68 | 9.58 | 5.33 | 15.5 | 9.96 | 35.1 | 0.0461 | 0.144 |
| 2 | 4.10 | 8.87 | 9.77 | 35.6 | 56.6 | 162 | 4.51 | 9.68 | 5.43 | 15.8 | 9.89 | 35.6 | 0.0447 | 0.143 |
| 3 | 4.18 | 8.88 | 9.95 | 36.1 | 57.3 | 155 | 4.69 | 9.56 | 5.48 | 15.6 | 10.8 | 35.1 | 0.0450 | 0.144 |
| 4 | 4.11 | 8.82 | 9.69 | 35.4 | 57.9 | 162 | 4.49 | 9.63 | 5.41 | 15.7 | 10.2 | 34.9 | 0.0449 | 0.142 |
| 5 | 4.16 | 9.12 | 9.90 | 35.1 | 56.5 | 153 | 4.43 | 9.68 | 5.44 | 15.6 | 10.1 | 35.6 | 0.0450 | 0.142 |
| 6 | 3.94 | 8.84 | 9.81 | 35.1 | 55.2 | 160 | 4.59 | 9.56 | 5.44 | 15.4 | 9.89 | 34.8 | 0.0450 | 0.141 |
| Average | 4.08 | 8.89 | 9.81 | 35.6 | 56.5 | 158 | 4.57 | 9.62 | 5.42 | 15.6 | 10.1 | 35.2 | 0.0451 | 0.143 |
| Recovered | 4.81 | | 25.8 | | 101 | | 5.05 | | 10.2 | | 25.0 | | 0.098 | |
| Spiked | 5.00 | | 25.0 | | 100 | | 5.00 | | 10.0 | | 25.0 | | 0.100 | |
| % Recovery | 96.3 | | 103.0 | | 101.0 | | 101.0 | | 101.8 | | 100.2 | | 97.6 | |

To evaluate the interference of the sample type on quantitation of analytes, a post column infusion experiment with an internal standard solution was performed concurrent with analysis of ten plasma samples extracted without internal standards. The suppression or enhancement of the internal standard signal at the retention time of the analytes was assessed by comparing to a blank extract of water. Three of the analytes, oleic acid, LGPC, and serine, demonstrated interference with the internal standard signal. The analytes LGPC and oleic acid showed modest signal suppression in the ten plasma samples. Since the co-eluting internal standards in this assay are isotopically-labeled, any mild sample type effect should occur similarly for the analyte and internal standard. By using the peak area ratio of the analyte to internal standard for quantitation, the sample type effect is thus compensated for in the final calculation.

However, due to its polarity, serine co-eluted with the compounds in the sample that were not retained by the reversed phase column (i.e., the solvent front), and showed significant signal suppression. Although the isotope-labeled internal standard should track serine for ionization, quantitation may still be affected by potentially co-eluting interference.

Figure 9:
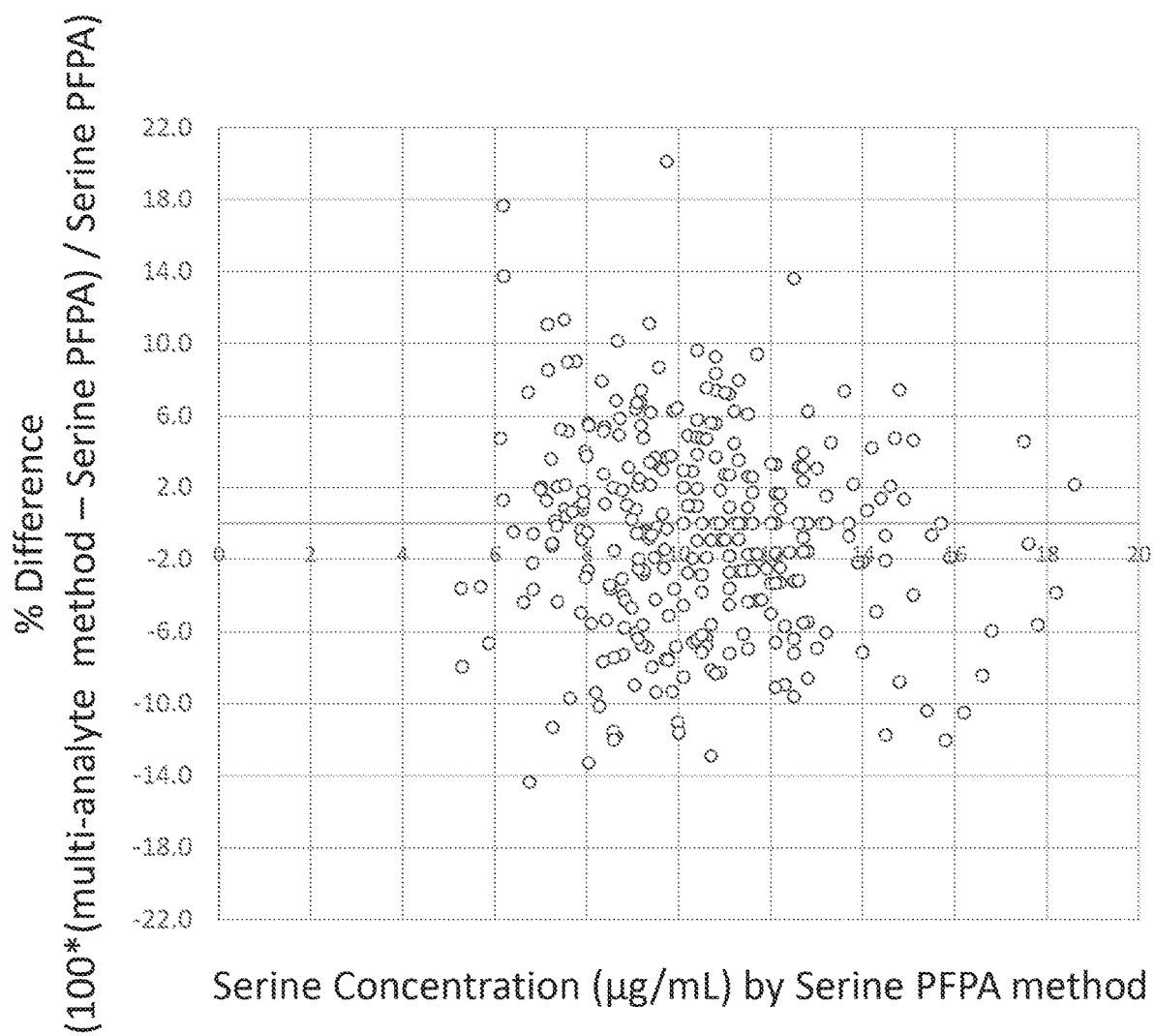
FIG. 9 shows a Bland-Altman plot comparing the quantitation of serine as determined using the method described herein to quantitate two or more analytes and the serine PFPA method.

Additional experiments were performed to address the accuracy of serine quantitation when using a multi-analyte in FIG. 9. The x-axis shows the concentration of serine when measured using the serine PFPA method. The y-axis shows the percent difference between the multi-analyte method and serine PFPA method, calculated as (100*(multi-analyte method—Serine PFPA)/Serine PFPA). For over 99% of the samples, the difference in serine quantitation between the serine PFPA method and the multi-analyte method was less than 14%, and no sample had a serine quantitation difference greater than 22%.

TABLE 10

Combinations of 2, 3, 4, 5, & 6 analytes are shown.

| Combination | 2-HB | 3-HB | 4-MOP | LGPC | oleic acid | pantothenate | serine |
|---|---|---|---|---|---|---|---|
| 1 | X | X | | | | | |
| 2 | X | | X | | | | |
| 3 | X | | | X | | | |
| 4 | X | | | | X | | |
| 5 | X | | | | | X | |
| 6 | X | | | | | | X |
| 7 | | X | X | | | | |
| 8 | | X | | X | | | |
| 9 | | X | | | X | | |
| 10 | | X | | | | X | |

TABLE 10-continued

Combinations of 2, 3, 4, 5, & 6 analytes are shown.

| Combination | 2-HB | 3-HB | 4-MOP | LGPC | oleic acid | pantothenate | serine |
|---|---|---|---|---|---|---|---|
| 11 |  | X |  |  |  |  | X |
| 12 |  | X | X |  |  |  |  |
| 13 |  | X |  | X |  |  |  |
| 14 |  | X |  |  | X |  |  |
| 15 |  | X |  |  |  |  | X |
| 16 |  |  | X | X |  |  |  |
| 17 |  |  | X |  | X |  |  |
| 18 |  |  | X |  |  | X |  |
| 19 |  |  |  | X | X |  |  |
| 20 |  |  |  | X |  | X |  |
| 21 |  |  |  |  | X | X |  |
| 22 | X | X | X |  |  |  |  |
| 23 | X | X |  | X |  |  |  |
| 24 | X | X |  |  | X |  |  |
| 25 | X | X |  |  |  | X |  |
| 26 | X | X |  |  |  |  | X |
| 27 | X |  | X | X |  |  |  |
| 28 | X |  | X |  | X |  |  |
| 29 | X |  | X |  |  | X |  |
| 30 | X |  | X |  |  |  | X |
| 31 | X |  |  | X | X |  |  |
| 32 | X |  |  | X |  | X |  |
| 33 | X |  |  | X |  |  | X |
| 34 | X |  |  |  | X | X |  |
| 35 | X |  |  |  | X |  | X |
| 36 | X |  |  |  |  | X | X |
| 37 |  | X | X | X |  |  |  |
| 38 |  | X | X |  | X |  |  |
| 39 |  | X | X |  |  | X |  |
| 40 |  | X | X |  |  |  | X |
| 41 |  | X |  | X | X |  |  |
| 42 |  | X |  | X |  | X |  |
| 43 |  | X |  | X |  |  | X |
| 44 |  | X |  |  | X | X |  |
| 45 |  | X |  |  | X |  | X |
| 46 |  | X |  |  |  | X | X |
| 47 |  |  | X | X | X |  |  |
| 48 |  |  | X | X |  | X |  |
| 49 |  |  | X | X |  |  | X |
| 50 |  |  | X |  | X | X |  |
| 51 |  |  | X |  | X |  | X |
| 52 |  |  | X |  |  | X | X |
| 53 |  |  |  | X | X | X |  |
| 54 |  |  |  | X | X |  | X |
| 55 |  |  |  | X |  | X | X |
| 56 |  |  |  |  | X | X | X |
| 57 | X | X | X | X |  |  |  |
| 58 | X | X | X |  | X |  |  |
| 59 | X | X | X |  |  | X |  |
| 60 | X | X | X |  |  |  | X |
| 61 | X | X |  | X | X |  |  |
| 62 | X | X |  | X |  | X |  |
| 63 | X | X |  | X |  |  | X |
| 64 | X | X |  |  | X | X |  |
| 65 | X | X |  |  | X |  | X |
| 66 | X | X |  |  |  | X | X |
| 67 | X |  | X | X | X |  |  |
| 68 | X |  | X | X |  | X |  |
| 69 | X |  | X | X |  |  | X |
| 70 | X |  | X |  | X | X |  |
| 71 | X |  | X |  | X |  | X |
| 72 | X |  | X |  |  | X | X |
| 73 | X |  |  | X | X | X |  |
| 74 | X |  |  | X | X |  | X |
| 75 | X |  |  | X |  | X | X |
| 76 | X |  |  |  | X | X | X |
| 77 |  | X | X | X | X |  |  |
| 78 |  | X | X | X |  | X |  |
| 79 |  | X | X | X |  |  | X |
| 80 |  | X | X |  | X | X |  |
| 81 |  | X | X |  | X |  | X |
| 82 |  | X | X |  |  | X | X |
| 83 |  | X |  | X | X | X |  |
| 84 |  | X |  | X | X |  | X |
| 85 |  | X |  | X |  | X | X |
| 86 |  | X |  |  | X | X | X |
| 87 |  |  | X | X | X | X |  |
| 88 |  |  | X | X | X |  | X |
| 89 |  |  | X | X |  | X | X |
| 90 |  |  | X |  | X | X | X |
| 91 |  |  |  | X | X | X | X |
| 92 | X |  | X | X | X | X |  |
| 93 | X |  | X | X | X |  | X |
| 94 | X |  | X | X |  | X | X |
| 95 | X |  | X |  | X | X | X |
| 96 | X |  |  | X | X | X | X |
| 97 | X | X |  | X | X | X |  |
| 98 | X | X |  | X | X |  | X |
| 99 | X | X |  | X |  | X | X |
| 100 | X | X |  | X |  | X | X |
| 101 | X | X | X |  | X | X |  |
| 102 | X | X | X |  | X |  | X |
| 103 | X | X | X |  |  | X | X |
| 104 | X | X | X | X |  | X |  |
| 105 | X | X | X | X |  |  | X |
| 106 | X | X | X | X | X |  |  |
| 107 |  | X | X | X | X | X |  |
| 108 |  | X | X | X | X | X |  |
| 109 |  | X | X | X | X | X |  |
| 110 |  | X | X | X | X |  | X |
| 111 |  | X | X | X |  | X | X |
| 112 |  | X | X | X |  |  | X |
| 113 | X | X |  | X | X | X |  |
| 114 | X |  | X | X | X | X | X |
| 115 | X | X |  | X | X | X | X |
| 116 | X | X | X |  | X | X | X |
| 117 | X | X | X | X |  | X | X |
| 118 | X | X | X | X | X |  | X |
| 119 |  | X | X | X | X | X | X |

What is claimed is:

1. A method for determining in a sample, by mass spectrometry, the amount of two or more analytes selected from the group consisting of alpha-hydroxybutyrate (2-HB), linoleoyl LPC (LGPC), oleic acid, 3-hydroxybutyrate (3-HB), 4-methyl-2-oxopentanoate (4-MOP), pantothenate, and serine, the method comprising:
   a) purifying a single injection of the sample by liquid chromatography;
   b) subjecting the single injection of the sample to an ionization source under conditions suitable to produce one or more ions detectable by mass spectrometry from each of the two or more analytes, wherein the analytes are not derivatized prior to ionization;
   c) measuring, by mass spectrometry, the amount of the two or more ions from each of the two or more analytes in the single injection of the sample, wherein the mass spectrometer is operated in negative mode; and
   d) using the measured amount of the two or more ions to determine the amount of each of the two or more analytes in the single injection of the sample;
      wherein at least one of the two or more analytes is selected from the group consisting of 2-HB, LGPC, 3-HB, 4-MOP, and oleic acid and a second of the two or more analytes is selected from the group consisting of serine and pantothenate.

2. The method of claim 1, wherein the two or more analytes comprise 2-HB and pantothenate.

3. The method of claim 1, wherein the two or more analytes comprise 2-HB and serine.

4. The method of claim 1, wherein the two or more analytes comprise LGPC and pantothenate.

5. The method of claim 1, wherein the two or more analytes comprise LGPC and serine.

6. The method of claim 1, wherein the amount 2-HB, LGPC, oleic acid, 3-HB, 4-MOP, pantothenate, and serine is determined.

7. The method of claim 1, wherein said liquid chromatography is selected from the group consisting of high performance liquid chromatography, ultra high performance liquid chromatography, and turbulent flow liquid chromatography.

8. The method of claim 1, wherein an internal standard is used to determine the amount of the two or more analytes in the sample.

9. The method of claim 8, wherein the internal standard comprises an isotopically labeled analogue of at least one of the two or more analytes to be measured.

10. The method of claim 1, wherein the sample comprises a biological sample.

11. The method of claim 10, wherein the sample is selected from the group consisting of blood, plasma and serum.

12. The method of claim 1, wherein at least one of the two or more analytes is selected from the group consisting of 2-HB and LGPC and a second of the two or more analytes is selected from the group consisting of serine and pantothenate.

13. The method of claim 12, wherein one of the two or more analytes is 2-HB and a second of the two or more analytes is selected from the group consisting of pantothenate, and serine.

14. The method of claim 12, wherein one of the two or more analytes is LGPC and a second of the two or more analytes is selected from the group consisting of pantothenate and serine.

15. The method of claim 1, wherein a run time for the method is less than 3 minutes.

* * * * *